(12) United States Patent
Amino et al.

(10) Patent No.: US 8,212,068 B2
(45) Date of Patent: Jul. 3, 2012

(54) ESTER DERIVATIVE AND USE THEREOF

(75) Inventors: Yusuke Amino, Kawasaki (JP); Yoshinobu Takino, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 619 days.

(21) Appl. No.: 12/237,142

(22) Filed: Sep. 24, 2008

(65) Prior Publication Data

US 2009/0170942 A1    Jul. 2, 2009

Related U.S. Application Data

(63) Continuation of application No. PCT/JP2007/056101, filed on Mar. 23, 2007.

(30) Foreign Application Priority Data

Mar. 24, 2006    (JP) ............................... 2006-084298

(51) Int. Cl.
   C07C 69/76    (2006.01)
   C07C 69/52    (2006.01)
   C07C 67/02    (2006.01)
(52) U.S. Cl. .......................... 560/55; 560/221; 560/254
(58) Field of Classification Search .................... None
   See application file for complete search history.

(56) References Cited

U.S. PATENT DOCUMENTS

| | | |
|---|---|---|
| 6,333,421 B1 | 12/2001 | Yazawa et al. |
| 2007/0020738 A1 | 1/2007 | Amino et al. |

FOREIGN PATENT DOCUMENTS

| | | |
|---|---|---|
| GB | 1032872 | 1/1965 |
| JP | 58-203939 | 11/1983 |
| JP | 2000-312598 | 11/2000 |
| JP | 3345744 B | 11/2002 |
| WO | WO 2005/099682 A1 | 10/2005 |

OTHER PUBLICATIONS

Database Caplus Chemical Abstracts Service, Columbus, Ohio, US; Database Accession No. 1995:997731, Abstract of Taniguchi et al.: EP 681825.*
Database Caplus Chemical Abstracts Service, Columbus, Ohio, US; Database Accession No. 1990:529324, Abstract of Zdero et al.: Phytochemistry (1990), 29(4), 1231-45.*
Database Caplus Chemical Abstracts Service, Columbus, Ohio, US; Database Accession No. 1997:628579, Abstract of Katagiri et al.: Phytochemistry (1997), 46(2), 347-352.*
Database Caplus Chemical Abstracts Service, Columbus, Ohio, US; Database Accession No. 2000:469941, Abstract of Murakami et al.: Cancer Letters (Shannon, Ireland) (2000), 157(1), 77-85.*
Database Caplus Chemical Abstracts Service, Columbus, Ohio, US; Database Accession No. 2002:106240, Abstract of Nomura et al.: Bioorganic & Medicinal Chemistry (2002), 10(4), 1069-1075.*
Grasso et al., Bioorganic Chemistry 35 (2007) 137-152.*
Database Caplus Chemical Abstracts Service, Columbus, Ohio, US; Database Accession No. 1966:11306, Abstract of NL 6500209.*
Database Caplus Chemical Abstracts Service, Columbus, Ohio, US; Database Accession No. 1976:99159, Abstract of Szolcsanyi et al., Arzneimittel-Forschung (1976), 26(1), 33-7.*
U.S. Appl. No. 12/345,249, filed Dec. 29, 2008, Amino et al.
U.S. Appl. No. 12/711,629, filed Feb. 24, 2010, Amino et al.
Jayaprakasam, et al., "Impact of Aklyl Esters of Caffeic and Ferulic Acids on Tumor Cell Proliferation, Cyclooxygenase Enzyme, and Lipid Peroxidation", Journal of Agricultural and Food Chemistry, published on web Jul. 1, 2006, 5375-5381, Compounds 18, 20, 22, p. 5377 "Synthesis of Ferulic Acid Esters."
Zdero, et al., "Diterpenes and other constituents from Pteronia species", Phytochemistry, 1990, 29(4), 1231-45, Compounds 42-45.
Kobata, et al., Novel Capsaicinoid-like substances, Capsiate and Dihydroc apsiate, from the Fruits of a Nonpungent Cultivar, Journal of Agricultural and Food Chemistry, 1998, vol. 46, No. 5, 1695-1697, p. 1696 Chemical Synthesis of 4-Hydroxy-3-methoxybenzyl-8-Methylnonanoate.
Giovanni Appendino, et al., "Chemoselective Esterification of Phenolic Acids and Alcohols", Organic Letters, vol. 4, No. 22, 2002, pp. 3839-3841.
Ahmed G. Hegazi, et al., "Egyptian Propolis: 3. Antioxidant, Antimicrobial Activities and Chemical Composition of Propolis from Reclaimed Lands", Zeitschrift für Naturforschung, vol. 57, 2002, pp. 395-402.

(Continued)

Primary Examiner — Karl J Puttlitz
(74) Attorney, Agent, or Firm — Oblon, Spivak, McClelland, Maier & Neustadt, L.L.P.

(57) ABSTRACT

A compound represented by the following formula (I')

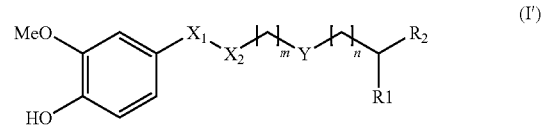

wherein $X_1$ is a methylene group, an ethylene group, a trimethylene group or a vinylene group, $X_2$ is a divalent group represented by the following formula A or B,

A:

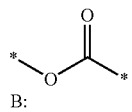

B:

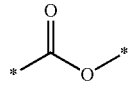

Y is an ethylene group or a vinylene group, m and n are each an integer of 0 to 7, which satisfy m+n=0 to 8, R1 and R2 are each independently a hydrogen atom, a methyl group or an ethyl group, provided that when $X_1$ is a methylene group, then $X_2$ is not a divalent group represented by the formula A, and when $X_1$ is a vinylene group, then $X_2$ is not a divalent group represented by the formula A. The compound is a stable capsinoid derivative, and is useful as an active ingredient of an external blood circulation enhancer or a cosmetic composition, a pharmaceutical composition, or a food composition.

26 Claims, No Drawings

OTHER PUBLICATIONS

Angélina Claude-Lafontaine, et al., "Volatile Constituents of the Flower Concrete of Gardenia Taitensis DC", Journal of Essential Oil research, vol. 4, No. 4, 1992, pp. 335-343.

Christopher S.J. Walpole, et al., "Analogues of Capsaicin with Agonist Activity as Novel Analgesic Agents; Structure-Activity Studies, 2. the Amide Bond B-Region", J. Med. Chem., vol. 36, 1993, pp. 2373-2380.

Cecilia Anselmi, et al., "Antioxidant Activity of Ferulic Acid Alkyl Esters in a Heterophasic System: A Mechanistic Insight", J. Agric. Food Chem. vol. 52, 2004, pp. 6425-6432.

* cited by examiner

ESTER DERIVATIVE AND USE THEREOF

Cross-Reference to Related Applications

The present application is a continuation of International patent application PCT/JP07/056101, filed on Mar. 23, 2007, which claims priority to Japanese patent application JP 2006-084298, filed on Mar. 24, 2006, which are incorporated herein by reference in their entireties.

TECHNICAL FIELD

The present invention relates to a novel ester derivative, use thereof, and a production method thereof. More particularly, the present invention relates to a novel ester derivative and a cosmetic composition, a pharmaceutical composition, a food composition and the like, which comprise the derivative as an active ingredient.

BACKGROUND ART

Capsaicin which is a natural pungent component contained in planta (hereinafter capsicums) belonging to *Capsicum* is known to have a blood circulation enhancing action resulting from a peripheral vasodilatory action. However, capsaicin is problematic in that it causes strong irritation. On the other hand, capsinoids such as capsiate, dihydrocapsiate and the like have been reported as analogues of capsaicinoids such as capsaicin and the like. Since these capsinoids cause less pungent irritation as compared to capsaicinoids, they are expected to be usable for diet foods and the like (patent reference 1, non-patent reference 1).

In addition, vanillyl nonanoate, which is a capsinoid, is known to show a blood circulation enhancing action during external application (patent reference 2). However, capsinoids, wherein vanillyl alcohol is esterified to fatty acid, are not entirely sufficient in the stability (J. Agric. Food. Chem. 2001, 49, 4026-4030), and a component having high stability has been desired from the aspects of formulation of preparations and the like.

As ester compound obtained by condensing alcohol or carboxylic acid having a vanillyl structure (3-methoxy-4-hydroxyphenyl group) with aliphatic carboxylic acid or long chain alcohol, some compounds are known besides the above-mentioned capsinoids. However, its physiological activities such as blood circulation enhancing action and the like have not been reported.

For example, there is a report on the synthesis the following compound (1) (non-patent reference 2). However, there is no report relating to the physiological activity of this compound.

(1)

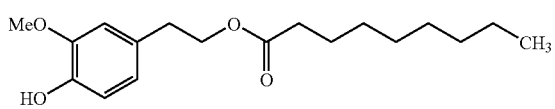

While there is a report on the following compound (2) (non-patent reference 3), and the antioxidant activity of this compound was examined. However, there is no report relating to its physiological activity such as blood circulation enhancing action and the like.

(2)

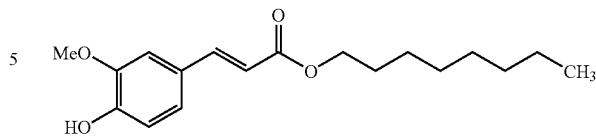

Moreover, there is a report on the following compound (3) (non-patent reference 4), and evaluation as an antipyretic analgesic agent has been performed. However, there is no report relating to its physiological activity such as blood circulation enhancing action and the like.

(3)

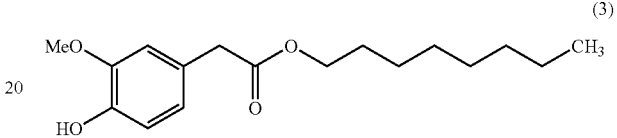

non-patent reference 1: JP-B-3345744
non-patent reference 2: WO2005/099682
non-patent reference 1: J. Agric. Food Chem., Vol. 46, No. 5 (1998), p. 1695-1697
non-patent reference 2: Organic Letters, Vol. 4, No. 22 (2002), p. 3839-3841
non-patent reference 3: J. Agric. Food Chem., Vol. 52, No. 21 (2004), p. 6425-6432
non-patent reference 4: J. Med. Chem., Vol. 36 (1993), p. 2373-2380

DISCLOSURE OF THE INVENTION

Problems to be Solved by the Invention

The present invention aims to provide a stable derivative of capsinoid and a composition comprising the derivative.

Means of Solving the Problems

The present inventors have conducted intensive studies in an attempt to solve the aforementioned problem and achieved stabilization by converting, in the molecular structure of capsinoids, the structure near the ester bond while maintaining the benzene ring structure derived from vanillyl alcohol. In addition, they have found that some of such compounds are not only stable as compared to natural capsinoids but also show a blood circulation enhancing action, which resulted in the completion of the present invention.

Accordingly, the present invention includes the following.
[1] A compound represented by the following formula (I)

(I)

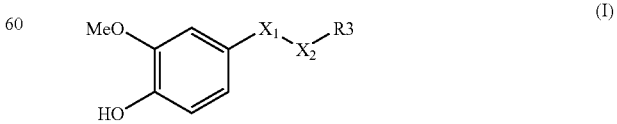

wherein $X_1$ is a methylene group, an ethylene group, a trimethylene group or a vinylene group, $X_2$ is a divalent group represented by the following formula A or B A:
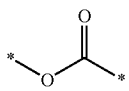

B:
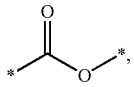

and
R3 is a group represented by the following formula (IIIa')

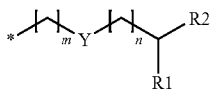
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group,
provided that
(1) when $X_1$ is an ethylene group and $X_2$ is a divalent group represented by the formula A, then R3 is not an n-octyl group;
(2) when $X_1$ is an ethylene group and $X_2$ is a divalent group represented by the formula B, then R3 is not an n-tridecanyl group;
(3) when $X_1$ is a methylene group, then $X_2$ is not a divalent group represented by the formula A;
(4) when $X_1$ is a methylene group and $X_2$ is a divalent group represented by the formula B, then R3 is not a straight chain alkyl group having a carbon number of 6 to 12;
(5) when $X_1$ is a vinylene group and $X_2$ is a divalent group represented by the formula B, then R3 is not a straight chain alkyl group; and
(6) when $X_1$ is a vinylene group, then $X_2$ is not a divalent group represented by the formula A (hereinafter to be also referred to as compound (I)).
[2] The compound of the above-mentioned [1], wherein m and n are each an integer of 0 to 7, which satisfy m+n=2 to 8.
[3] The compound of the above-mentioned [1] or [2], wherein $X_1$ is an ethylene group or a trimethylene group, and $X_2$ is a divalent group represented by the formula A.
[4] The compound of the above-mentioned [1] or [2], wherein $X_1$ is a methylene group or an ethylene group, and $X_2$ is a divalent group represented by the formula B.
[5] The compound of the above-mentioned [1] or [2], wherein $X_1$ is a methylene group, and $X_2$ is a divalent group represented by the formula B.
[6] The compound of any of the above-mentioned [2] to [5], wherein Y is an ethylene group, and R1 and R2 are each independently a methyl group or an ethyl group.
[7] An external blood circulation enhancer comprising one or more kinds of a compound represented by the following formula (I')

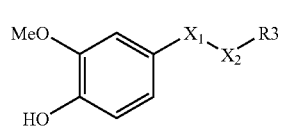
(I')

wherein $X_1$ is a methylene group, an ethylene group, a trimethylene group or a vinylene group, $X_2$ is a divalent group represented by the following formula A or B A:
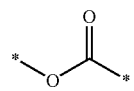

B:
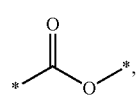

and
R3 is a group represented by the following formula (IIIa')

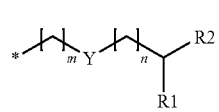
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group,
provided that
(3) when $X_1$ is a methylene group, then $X_2$ is not a divalent group represented by the formula A, and
(6) when $X_1$ is a vinylene group, then $X_2$ is not a divalent group represented by the formula A.
(hereinafter also referred to as compound (I')).
[8] The external blood circulation enhancer of the above-mentioned [7], wherein m and n are each an integer of 0 to 7, which satisfy m+n=2 to 8.
[9] The external blood circulation enhancer of the above-mentioned [7] or [8], wherein $X_1$ is an ethylene group or a trimethylene group, and $X_2$ is a divalent group represented by the formula A.
[10] The external blood circulation enhancer of the above-mentioned [7] or [8], wherein $X_1$ is a methylene group or an ethylene group, and $X_2$ is a divalent group represented by the formula B.
[11] The external blood circulation enhancer of the above-mentioned [7] or [8], wherein $X_1$ is a methylene group, and $X_2$ is a divalent group represented by the formula B.
[12] The external blood circulation enhancer of any of the above-mentioned [7] to [11], wherein Y is an ethylene group, and R1 and R2 are each independently a methyl group or an ethyl group.
[13] A cosmetic composition comprising the external blood circulation enhancer of any of the above-mentioned [7] to [12].
[14] A sympathetic activation pharmaceutical composition comprising one or more kinds of compound (I').

[15] The sympathetic activation pharmaceutical composition of the above-mentioned [14], wherein m and n are each an integer of 0 to 7, which satisfy m+n=2 to 8.

[16] A sympathetic activation food composition comprising one or more kinds of compound (I').

[17] The sympathetic activation food composition of the above-mentioned [16], wherein m and n are each an integer of 0 to 7, which satisfy m+n=2 to 8.

[18] A production method of compound (I'), comprising subjecting an alcohol derivative represented by the following formula (II)

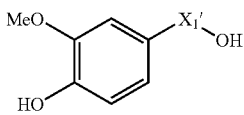
(II)

wherein $X_1'$ is an ethylene group or a trimethylene group, to a dehydration condensation reaction with at least one selected from the group consisting of a fatty acid represented by the following formula (IIIa)

HO₂C—R3   (IIIa)

wherein R3 is a group represented by the following formula (IIIa')

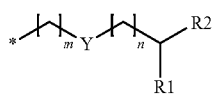
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, a fatty acid ester represented by the following formula (IIIb)

R4-O₂C—R3   (IIIb)

wherein R4 is an aliphatic hydrocarbon group and R3 is as defined above, and a triglyceride represented by the following formula (IIIc)

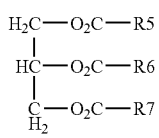
(IIIc)

wherein at least one of R5, R6 and R7 is a group represented by the above-mentioned formula (IIIa'), and the rest are each independently an aliphatic hydrocarbon group, in the presence of an enzyme catalyst, or subjecting a carboxylic acid derivative represented by the following formula (IV)

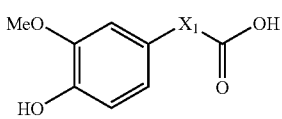
(IV)

wherein $X_1$ is a methylene group, an ethylene group, a trimethylene group or a vinylene group, or a carboxylate represented by the following formula (IV')

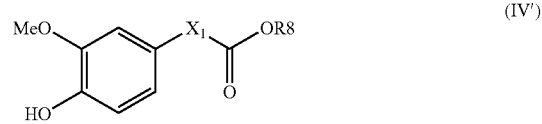
(IV')

wherein $X_1$ is as defined above and R8 is an aliphatic hydrocarbon group, to a dehydration condensation reaction with an aliphatic alcohol represented by the following formula (V)

HO—R3   (V)

wherein R3 is as defined above, in the presence of an enzyme catalyst.

[19] A production method of compound (I'), comprising subjecting an alcohol derivative represented by the following formula (II)

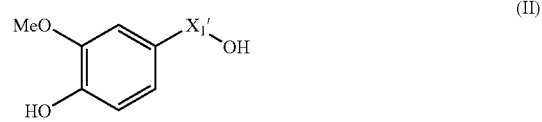
(II)

wherein $X_1'$ is an ethylene group or a trimethylene group, to a chemical condensation reaction with a fatty acid represented by the following formula (IIIa)

HO₂C—R3   (IIIa)

wherein R3 is a group represented by the following formula (IIIa')

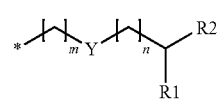
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, using a dehydrating condensation agent, or subjecting a carboxylic acid derivative represented by the formula (IV)

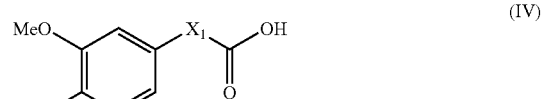
(IV)

wherein $X_1$ is a methylene group, an ethylene group, a trimethylene group or a vinylene group, to a chemical condensation reaction with an aliphatic alcohol represented by the following formula (V)

HO—R3   (V)

wherein R3 is as defined above, using a dehydrating condensation agent.

[20] A production method of a compound represented by the following formula (I″)

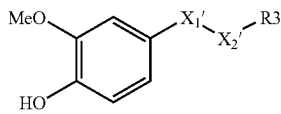

wherein $X_2'$ is a divalent group represented by the following formula A

A:

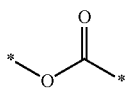

R3 is a group represented by the following formula (IIIa')

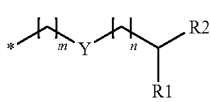

wherein Y is an ethylene group or a vinylene group, m and n are each an integer of 0 to 7, which satisfy m+n=0 to 8, and R1 and R2 are each independently a hydrogen atom, a methyl group or an ethyl group, and
$X_1'$ is an ethylene group or a trimethylene group, which comprises converting a fatty acid represented by the following formula (IIIa)

$HO_2C$—R3  (IIIa)

wherein R3 is as defined above, to an acid chloride, and reacting the acid chloride with an alcohol derivative represented by the following formula (II)

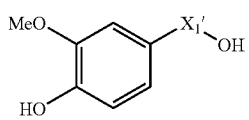

wherein $X_1'$ is as defined above, in the presence of a base.

Effect of the Invention

The present invention provides stable novel capsinoid analogs and consequently provides safe and promising cosmetics, pharmaceutical agents, diet foods and the like, which have a blood circulation enhancing action and a sympathetic activation action.

BEST MODE FOR CARRYING OUT THE INVENTION

The present invention is explained in detail in the following.

Examples of the aliphatic hydrocarbon group for R4 and the like include a straight chain or branched chain alkyl group having a carbon number of 1 to 6 (e.g., methyl, ethyl, n-propyl, isopropyl, n-butyl, isobutyl, sec-butyl, tert-butyl, n-pentyl, isopentyl, neopentyl, 1-ethylpropyl, n-hexyl, isohexyl, 1,1-dimethylbutyl, 2,2-dimethylbutyl, 3,3-dimethylbutyl etc.) or a straight chain or branched chain alkenyl group having a carbon number of 2 to 6 (e.g., vinyl, allyl, isopropenyl, 2-methylallyl, 1-propenyl, 2-methyl-1-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl etc.) Among these, methyl, ethyl and vinyl are preferable.

The novel compound found by the present invention is a compound represented by the following formula (I).

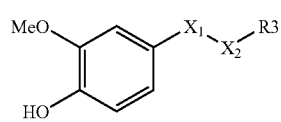

wherein $X_1$ is a methylene group, an ethylene group, a trimethylene group or a vinylene group,
$X_2$ is a divalent group represented by the following formula A or B

A:

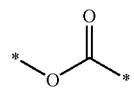

B:

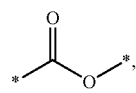

and
R3 is a group represented by the following formula (IIIa')

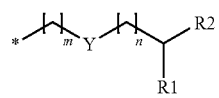

wherein Y is an ethylene group or a vinylene group, m and n are each an integer of 0 to 7, which satisfy m+n=0 to 8, and R1 and R2 are each independently a hydrogen atom, a methyl group or an ethyl group.

Compound (I) characteristically has a chemical structure wherein the structure near the ester of capsinoids is converted.

However, in the above-mentioned formula (I), structures of the compounds defined by the following conditions (1) to (5) are disclosed in known references, although the functions thereof are different from those in the field of the present invention:

(1) a compound wherein $X_1$ is an ethylene group, $X_2$ is a divalent group represented by the formula A, and R3 is an n-octyl group;
(2) a compound wherein $X_1$ is an ethylene group, $X_2$ is a divalent group represented by the formula B, and R3 is an n-tridecanyl group;
(3) a compound wherein $X_1$ is a methylene group, and $X_2$ is a divalent group represented by the formula A;

(4) a compound wherein $X_1$ is a methylene group, $X_2$ is a divalent group represented by the formula B, and R3 is a straight chain alkyl group having a carbon number of 6 to 12; and
(5) a compound wherein $X_1$ is a vinylene group, $X_2$ is a divalent group represented by the formula B, and R3 is a straight chain alkyl group.

To avoid coincidence, these compounds are excluded by the proviso.

In the formula (I), moreover, a compound defined by the following conditions (6) is considered to be chemically unstable since it has an enol ester structure, and difficult to synthesize. Therefore, the compound is excluded from the compound of the present invention by the proviso.

(6) A compound wherein $X_1$ is a vinylene group, and $X_2$ is a divalent group represented by the formula A.

Preferable concrete examples of compound (I) include a fatty acid ester of homovanillyl alcohol and 3-(3-methoxy-4-hydroxyphenyl)propanol, which is a compound of the aforementioned formula (I) wherein $X_2$ is a divalent group represented by the formula A, namely, a compound represented by the following formula (I-a)

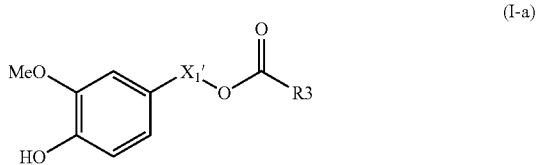

(I-a)

in the above-mentioned formula I-a, R3 is as defined for R3 in the aforementioned formula (I), and $X_1'$ is an ethylene group or a trimethylene group, or a fatty acid ester of homovanillic acid, 3-(3-methoxy-4-hydroxyphenyl)propionic acid and ferulic acid, which is a compound of the aforementioned formula (I), wherein $X_2$ is a divalent group represented by the formula B, namely, a compound represented by the following formula (I-b)

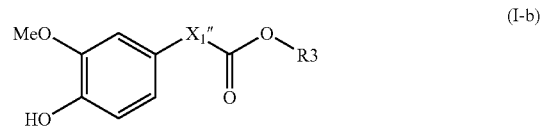

(I-b)

in the above-mentioned formula I-b, R3 is as defined for R3 in the aforementioned formula (I), and $X_1''$ is a methylene group, an ethylene group or a vinylene group (more preferably methylene group or ethylene group).

In addition, particularly preferable concrete examples of compound (I) include a fatty acid ester of homovanillic acid, which is a compound of the above-mentioned formula (I-b) wherein $X_1$ is a methylene group.

More preferable concrete examples of the aforementioned compound (I) include an ester wherein R3 moiety is a saturated or unsaturated straight chain or branched chain aliphatic group having a carbon number of 3 to 15, preferably 5 to 14, which is still more preferably an ester wherein R3 moiety is a saturated or unsaturated branched aliphatic group corresponding to a branched fatty acid side chain of capsaicinoids included in capsicums. For example, a compound wherein R3 is represented by the above-mentioned formula (IIIa') wherein Y is an ethylene group, and R1 and R2 are each independently a methyl group or an ethyl group (that is, R3 moiety is a saturated branched chain fatty acid side chain) is preferable, and a compound wherein m and n are each an integer of 0 to 5, which satisfy m+n=0 to 6 (that is, a compound wherein R3 moiety has a carbon number of 5 to 10) is further preferable.

Specific examples of the ester derivative wherein the R3 moiety corresponds to a branched fatty acid side chain of capsaicinoids are shown in the following Table 1.

TABLE 1

| structure | fatty acid part (R3—COOH) or aliphatic alcohol part (R3—OH) | Name of fatty acid part Name of aliphatic alcohol part |
|---|---|---|
| Representative structures of novel ester derivatives | | |

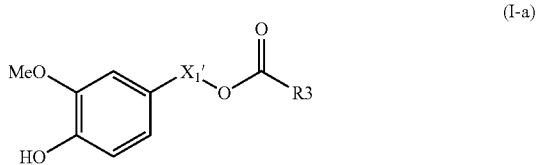

TABLE 1-continued

Representative structures of novel ester derivatives

| structure | fatty acid part (R3—COOH) or aliphatic alcohol part (R3—OH) | Name of fatty acid part / Name of aliphatic alcohol part |
|---|---|---|
| 4. | | (E)-6-methyl-4-heptenoic acid<br>(E)-5-methyl-3-hexenol |
| 5. | | (E)-7-methyl-5-octenoic acid<br>(E)-6-methyl-4-heptenol |
| 6. | | (E)-8-methyl-6-decenoic acid<br>(E)-7-methyl-5-nonenol |
| 7. | | (E)-9-methyl-6-decenoic acid<br>(E)-8-methyl-5-nonenol |
| 8. | | (E)-9-methyl-7-decenoic acid<br>(E)-8-methyl-6-nonenol |
| 9. | | (E)-10-methyl-8-undecenoic acid<br>(E)-9-methyl-7-decenol |
| 10. | | (E)-11-methyl-9-dodecenoic acid<br>(E)-10-methyl-8-undecenol |
| 11. | | 8-methylnonanoic acid<br>7-methyloctanol |
| 12. | | 7-methyloctanoic acid<br>6-methylheptenol |
| 13. | | 6-methylheptanoic acid<br>5-methylhexanol |
| 14. | | 5-methylhexanoic acid<br>4-methylpentanol |
| 15. | | 4-methylpentanoic acid<br>3-methylbutanol |
| 16. | | (S)-7-methylnonanoic acid<br>(S)-6-methyloctanol |
| 17. | | (E)-8-methyl-6-nonenoic acid<br>(E)-7-methyl-5-octenol |

Other embodiments of the present invention include an external blood circulation enhancer comprising one or more kinds of a compound represented by the following formula (I')

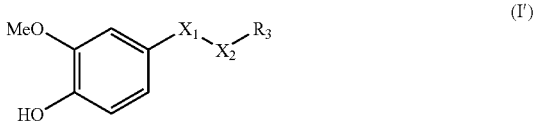

wherein $X_1$ is a methylene group, an ethylene group, a trimethylene group or a vinylene group, $X_2$ is a divalent group represented by the following formula A or B

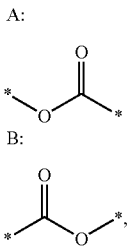

and
R3 is a group represented by the following formula (IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that
(3) when $X_1$ is a methylene group, then $X_2$ is not a divalent group represented by the formula A, and
(6) when $X_1$ is a vinylene group, then $X_2$ is not a divalent group represented by the formula A, and a cosmetic composition comprising the same.

In other words, since compound (I') of the present invention has a blood circulation enhancing action also in external use, it is useful as an active ingredient of cosmetics.

In addition, compound (I') of the present invention is assumed to have a capsaicin receptor-stimulating activity. Therefore, compound (I') of the present invention is considered to have, in addition to the aforementioned external blood circulation enhancing action, various physiological activities similar to those of capsaicinoids, such as sympathetic activation action, energy metabolism enhancing action, immunostimulatory action, lipolysis enhancing action, antiobesity action, body fat accumulation suppressive action, oral blood circulation enhancing action, analgesic action and the like. As such, compound (I') of the present invention is considered to be also useful as an active ingredient of a pharmaceutical agent or a food additive.

Here, a capsaicin receptor is also called VR1 or TRPV1 (Transient Receptor Potential Vanilloid Receptor 1).

For measurement of the capsaicin receptor stimulating activity, for example, according to the following method, compound (I') of the present invention is brought into contact with a cell system that expresses TRPV1 and activation of TRPV1 is measured, whereby the sympathetic activation action of compound (I') of the present invention can be easily confirmed.

Measurement of Capsaicin Receptor Stimulating Activity

A cell system that expresses TRPV1 can be obtained, for example, by transforming various cell lines such as *Xenopus oocyte*, chinese hamster ovary cell (CHO), BHK (baby hamster kidney) cell, HEK (human embryonic kidney) cell, Sf-9 insect cell, PC12 cell, CACO-2 cell and the like with a vector containing a gene encoding TRPV1 and the like (Michael J. Caterina, et al., Nature, 1997; 389, 816-824). In addition, when DNA encoding TRPV1 is to be incorporated into chromosome DNA to achieve permanent expression of TRPV1, the above-mentioned cells except *Xenopus oocyte* can be used. A DNA encoding TRPV1 can be introduced into these cells by a known method. The techniques necessary for the operations such as introduction of DNA encoding TRPV1 into the cell and the like are described in Sambrook, J., Fritsch, E. F., and Maniatis, T., "Molecular Cloning A Laboratory Manual, Second Edition", Cold Spring Harbor Laboratory Press, (1989) and the like.

TRPV1 may be a protein derived from mammals such as human, monkey, rat, mouse, dog, bovine, rabbit and the like, birds, fish or any other animal, and may be a variant thereof, as long as it accepts capsaicin or capsinoid and induces current change or membrane potential change, such as calcium, sodium and the like. The amino acid sequences of TRPV1 are registered under Accession nos.: CAB89866 (human), NP_058903 (rat) in GenBank. In addition, the base sequences of a gene encoding TRPV1 are registered under Accession nos.: AJ272063 (human), NM_017207 (rat) in GenBank. The base sequence encoding human TRPV1 is shown in SEQ ID NO: 1, and the amino acid sequence of human TRPV1 is shown in SEQ ID NO: 2.

The activation of TRPV1 can be measured, for example, by contacting compound (I') with a cell made to express TRPV1, and measuring the second messenger resulting from the binding of compound (I') to VR1, a membrane potential change and the like. The method of measuring the second messenger includes, for example, measurement of change of intracellular calcium concentration and the like. In addition, the activation of TRPV1 can also be measured by contacting compound (I') and TRPV1 against with a cell made to express TRPV1, measuring the membrane potential resulting from the binding of TRPV1 agonist to TRPV1, and measuring a membrane potential change due to the absence or presence of compound (I'). Here, the TRPV1 agonist also includes TRPV1 ligand.

Instead of detecting the second messenger, it is also possible to measure activation of TRPV1 by, using labeled known TRPV1 agonist, measuring the labeled agonist—TRPV1 binding, and detecting inhibition of the aforementioned binding by compound (I').

Examples of the TRPV1 agonist include capsaicin, olvanil, and capsinoid. Examples of the capsinoid include capsiate, dihydrocapsiate, nordihydrocapsiate and capsiate derivatives such as vanillyl decanoate, vanillyl nonanoate, vanillyl octanoate and the like, and fatty acid esters of vanillyl alcohol and various straight chain or branched chain fatty acids which have a fatty acid chain length similar to that of nordihydrocapsiate. Capsiate (4-hydroxy-3-methoxybenzyl (E)-8-methyl-6-nonenoate, hereinafter to be sometimes abbreviated as "CST"), dihydrocapsiate (4-hydroxy-3-methoxybenzyl 8-methylnonanoate, hereinafter to be sometimes abbreviated "DCT"), and nordihydrocapsiate (4-hydroxy-3-methoxybenzyl 7-methyl-octanoate, hereinafter to be sometimes abbreviated as "NDCT") respectively have the following chemical formulas.

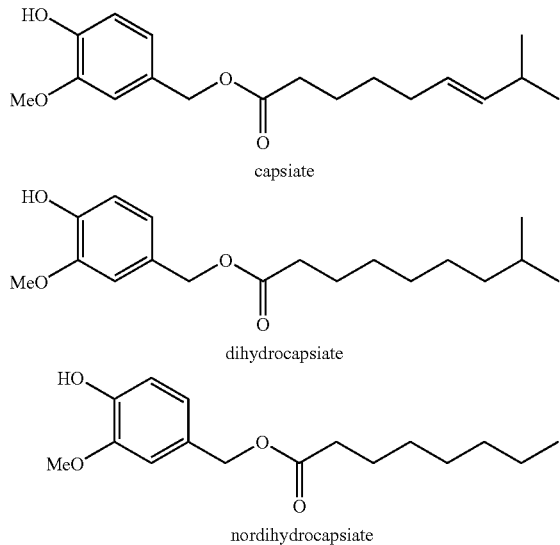

capsiate dihydrocapsiate nordihydrocapsiate

When compound (I') of the present invention is used as an active ingredient such as an external blood circulation enhancer, a sympathetic activation agent and the like of cosmetics, pharmaceutical agents and foods, the compound group represented by the aforementioned formula (I') includes, in addition to compound (I), various ester derivatives defined by the above-mentioned (1), (2), (4) and (5), which were removed in the above-mentioned section of compound (I) having known structures.

In the formula (I), a compound defined by the above-mentioned (3) encompasses capsinoids such as capsiate and the like, and a compound defined by the above-mentioned (6) is feared for poor stability. Hence, they are not encompassed in compound (I').

Specific examples of compound (I'), preferable embodiments and the like are similar to those of compound (I).

The cosmetic composition comprising the external blood circulation enhancer of the present invention may concurrently contain conventionally-employed blood circulation enhancers where appropriate. Examples of such blood circulation enhancers include powdered *capsicum, capsicum* tincture, *capsicum* essence, capsaicin, homocapsaicin, homodihydrocapsaicin, vanillyl nonanamide and the like, ginger extract, *capsicum* extract, nicotinic acid, sophorae radix extract, *Astragalus* root extract, *zingiber siccatum* extract, safflower extract, Japanese pepper extract, *Salvia miltiorrhiza* extract, panacis japonici rhizoma extract, ginseng extract, γ-aminobutyric acid (GABA) and the like.

Furthermore, the cosmetic composition of the present invention may contain various components generally used as cosmetic or skin external preparations as long as the effect of the present invention is not inhibited. Examples of such components include oily base, surfactant, polymeric substance, solvent, powder substance, antioxidant, anti-inflammatory agent, UV absorber, skin-lightening agent, cellular stimulant, moisturizing agent, metal chelating agent dyes, flavor, transdermal absorption enhancer and the like.

Examples of the oily base include hydrocarbons such as squalane, liquid paraffin, light liquid isoparaffin, heavy liquid isoparaffin, microcrystalline wax, solid paraffin and the like, silicones such as dimethicone, phenyldimethicone, cyclomethicone, amodimethicone, polyether-modified silicones and the like, esters such as jojoba oil, carnauba wax, rhus succedanea fruit wax, beeswax, whale wax, octyldodecyl oleate, isopropyl myristate, neopentylglycol diisostearate, diisostearyl malate and the like, fatty acids such as stearic acid, lauric acid, myristic acid, palmitic acid, isostearic acid, isopalmitic acid, behenic acid, oleic acid and the like, acylamino acids such as acylglutamic acid, acylglycine, acylalanine, acylsarcosine and the like, higher alcohols such as behenyl alcohol, cetyl alcohol, oleyl alcohol, octadecyl alcohol and the like, triglycerides such as castor oil, coconut oil, hydrogenated coconut oil, camellia Japonica oil, wheatgerm oil, glycelyl triisostearate, glycelyl isooctanoate, olive oil etc., and the like.

Examples of the surfactant include nonionic surfactants such as sorbitan sesquioleate, sorbitan monooleate, sorbitan trioleate, sorbitan sesquistearate, sorbitan monostearate, sorbitan polyoxyethylene monooleate, sorbitan polyoxyethylene monostearate, polyoxyethylene stearate, polyoxyethylene oleate, polyoxyethylene glycerol fatty acid ester, polyoxyethylene alkylether, polyoxyethylene hydrogenated castor oil and the like, anionic surfactants such as sodium lauryl stearate, polyoxyethylenealkyl sulfate, sulfosuccinate salt, acylglutamate salt, acylsarcosinate salt, acylglycinate salt, acylalaninate salt and the like, cationic surfactants such as quaternary alkylammonium salt and the like, amphoteric surfactants such as alkylbetaine and the like, emulsifiers, solubilizers and the like.

Examples of the solvent include lower alcohols such as ethanol and the like, polyvalent alcohols such as 1,2-pentanediol, 1,2-hexyleneglycol, isopreneglycol and the like, ethers and the other organic solvents, water and the like.

Examples of the polymeric substance include polyamino acids such as polyaspartic acid, ε-polylysine, γ-polyglutamic acid and the like and derivatives thereof, natural polymeric compounds such as collagen, elastin and the like, semisynthetic polymer compounds such as partially deacetylated chitin and the like, synthetic polymer compounds such as carboxymethylcellulose etc., and the like.

Examples of the powder substance include organic powders such as crystalline cellulose, crosslinking methylpolysiloxane, polyethylene powder, acrylic resin powder and the like, inorganic powders (optionally surface-treated as appropriate) such as talc, mica, sericite, magnesium carbonate, calcium carbonate, titanium dioxide, iron oxide, iron blue, ultramarine blue, titanium mica, titanium sericite, silica and the like, pearlescent pigments such as hybrid fine powder (hybrid fine powder), titanium dioxide-coated mica and the like, polymer powders such as photochromic pigment, nylon powder and the like, organic powders such as N-ε-lauroyllysine etc., and the like.

Examples of the dye include legal tar dye first category, legal tar dye second category, legal tar dye third category, hair dye, natural dye, mineral dye and the like.

Examples of the flavor include animal flavor such as musk and the like, plant flavors such as jasmine oil and the like, synthetic flavors such as α-amylcinnamaldehyde and the like, blended flavors and the like.

Examples of the transdermal absorption enhancer include urea, 2-pyrrolidone, 1-hexanol, 1-octanol, 1-decanol, 1-menthol, sodium lauryl sulfate, isopropyl myristate, n-hexyl acetate, oleic acid and the like.

The external blood circulation enhancer of the present invention can be added as an active ingredient of cosmetics for skin and hair, bathwater additives or toiletry products by adding, where necessary, the aforementioned various other components according to a conventional method. The dosage form thereof is not particularly limited, and can take any dosage form such as solution state, paste state, gel state, solid state, powder state and the like. Examples thereof include oil, lotion, cream, emulsion, gel, shampoo, hair rinse, hair conditioner, enamel, foundation, lipstick, face powder, pack, ointment, granule, capsule, perfume, powder, cologne, toothpaste, soap, aerosol, cleansing foam and the like. Furthermore, the external blood circulation enhancer of the present invention can also be used for pharmaceutical agents or quasi-drugs for the prevention or improvement of various dermatic diseases, such as hair-growth medicine, an agent for antiaging and improving skin, skin essence, an agent for preventing and improving skin roughness due to capped skin•crack and the like.

While the content of the external blood circulation enhancer of the present invention in cosmetic compositions also varies depending on the kind of component, it only needs to be contained at a level permitting provision of a desired blood circulation improving effect, which is, for example, about 0.01 to 10 wt % of the cosmetic composition.

Here, when compound (I') of the present invention is used as a component of cosmetics, pharmaceutical agents and foods, only one kind of compound (I') may be contained, or a mixture of two or more kinds of compound (I') may also be contained.

A pharmaceutical composition containing compound (I') of the present invention is also useful as a sympathetic activation agent, and can also be used as a therapeutic agent such as an antiobesity agent, an immunostimulant, a blood circulation enhancer, an analgesic, an antipruritic and the like.

When compound (I') of the present invention is used as a component of a pharmaceutical composition, the form of the pharmaceutical composition is not particularly limited, and any optional dosage form known in this technical field can be employed.

Examples thereof include oral preparation such as solid preparation, liquid agent and the like, parenteral preparations such as subcutaneous, intramuscular or intravenous injection, adhesive preparation, suppository, inhalant and the like. All of them can be produced according to methods known per se in this technical field.

Examples of the solid preparation include, but are not limited to, powder, granule, tablet, pill, capsule, troche, suppository and the like for oral administration, and examples of the liquid agent include, but are not limited to, solution, syrup, emulsion, suspension, inhalant and the like.

The content of compound (I') in the pharmaceutical composition is appropriately determined to achieve a suitable dose within the indicated range.

The pharmaceutical composition comprising compound (I') of the present invention can contain, where necessary, carrier, excipient, binder, swelling agent, lubricant, flowability improving agent, lubricant, sweetening agent, flavor, preservative, antioxidant, coating agent, various vitamins, various amino acids and the like.

Specific examples of the components which can be contained in the pharmaceutical composition of the present invention include excipients such as microcrystalline cellulose, crystalline cellulose, lactose, corn starch, sucrose, glucose; binders such as tragacanth, gum arabic, corn starch, gelatin, polyvinyl alcohol, polyvinyl ether, ethylcellulose, methylcellulose, shellac, hydroxypropylcellulose, hydroxypropyl starch, polyvinylpyrrolidone; swelling agents such as corn starch, pregelatinated starch, alginic acid, dextrin; lubricants such as magnesium stearate; flowability improving agents such as fine silicon dioxide; lubricants such as glyceryl fatty acid ester, magnesium stearate, talc, polyethylene glycol, silica, hydrogenated vegetable oil; sweetening agents such as sucrose, lactose, aspartame, acesulfame-K, sucralose, monatin, stevia, saccharin and the like; flavors to be used for various foods such as peppermint, vanilla flavor, cherry, raspberry ketone and the like; preservatives such as paraoxybenzoates, chlorobutanol, benzyl alcohol, sorbic acid and the like; antioxidants such as sulfite, ascorbic acid, vitamin E, butylhydroxytoluene, sodium sulfite; coating agents such as shellac, sucrose, gelatin, hydroxypropylcellulose etc., and the like.

While the dose of compound (I') of the present invention varies depending on the kind of disease, pathology, age and administration form, it is generally 0.01 mg to 20 g, preferably about 0.1 mg to 10 g, per day for an adult, which can be administered at once or in several portions.

The food composition of the present invention is useful as a sympathetic activation food, and is considered to particularly contribute to the promotion of fat burn by its sympathetic activation action. Thus, it can be preferably used as a food for diet purposes.

The "food" in the present invention refers to food in general, and includes, in addition to general foods including what is called health foods, such as food for specified health uses and food with nutrient function claims, which are defined in food with health claims system of the Ministry of Health, Labour and Welfare, and further includes dietary supplements.

The form of the food composition of the present invention is not particularly limited, and may be any as long as it permits oral ingestion.

Examples thereof include powder, granule, tablet, hard capsule, soft capsule, liquid (drinks, jelly drinks etc.), candy, chocolate and the like, all of which can be produced by a method known per se in this technical field.

The content of compound (I') in the food composition is appropriately determined to achieve a suitable dose within the indicated range.

Other food additives can be used as necessary for the food composition of the present invention. Examples of such food additive include fruit juice, dextrin, cyclic oligosaccharide, saccharides (monosaccharides such as fructose, glucose etc. and polysaccharides), acidulant, flavor, Hiki cha powder and the like for adjusting and improving taste, emulsifier, collagen, powdered milk, polysaccharide thickener, agar and the like for improving texture, and further, those generally used as components for general health foods and the like, such as vitamins, egg shell calcium, calcium pantothenate, other minerals, royal jelly, propolis, honey, dietary fibre, *Agaricus subrufescens*, chitin, chitosan, flavonoids, carotenoids, lutein, herbal medicine, chondroitin, various amino acids and the like.

Compound (I') of the present invention can be produced by subjecting an alcohol derivative represented by the formula (II) and fatty acid represented by the formula (IIIa) or fatty acid ester thereof and the like, to a dehydration condensation reaction by an enzyme catalyst (lipase etc.), or by subjecting a carboxylic acid derivative represented by the formula (IV) or carboxylate thereof and aliphatic alcohol represented by the formula (V) to a dehydration condensation reaction by an enzyme catalyst (lipase etc.).

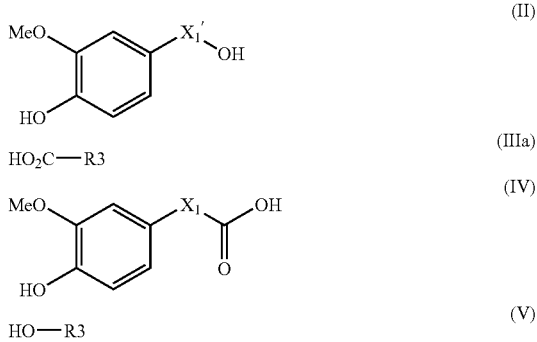

wherein each symbol is as defined above.

In addition, compound (I') can be produced by subjecting an alcohol derivative represented by the formula (II) and fatty acid represented by the formula (IIIa) to a chemical condensation reaction with a dehydrating condensation agent, or subjecting a carboxylic acid derivative represented by the formula (IV) and aliphatic alcohol represented by the formula (V) to a chemical condensation reaction with a dehydrating condensation agent. Examples of the dehydrating condensation agent include EDC [1-ethyl-3-(3-dimethylaminopropyl)carbodiimide hydrochloride] or DCC (N,N-dicyclohexylcarbodiimide) with DMAP (4-dimethylaminopyridine), DEAD (diethyl azodicarboxylate) or DIAD (diisopropyl azodicarboxylate) with triphenylphosphine and the like.

Moreover, a compound represented by the formula (I″), namely, a compound of the formula (I') wherein $X_1$ is an ethylene group or a trimethylene group, and $X_2$ is a divalent group represented by the formula A can also be produced, for example, by a synthesis method based on chemical reactions wherein fatty acid represented by the formula (IIIa) is once converted to acid chloride, followed by reaction with an alcohol derivative represented by the formula (II) in the presence of a base.

While a dehydration condensation reaction using lipase as an enzyme catalyst is explained in the following, the production method is not limited thereto.

Compound (I') can be produced by a dehydration condensation by lipase of an alcohol derivative (II) and a corresponding fatty acid component and/or an ester form thereof, or aliphatic alcohol (V) and a carboxylic acid derivative (IV) and/or an ester form thereof in a solvent. The order of addition is not particularly limited.

The lipase to be used as the reaction catalyst may be any as long as it can catalyze this reaction, and lipases derived from microorganisms, animals or plants can be used without limitation. These lipases can be used alone or in a mixture thereof. From the aspects of re-use, such lipase is preferably immobilized by a conventional method to be used.

Particularly, lipase derived from microorganism is preferable. Specific examples include lipases derived from the genus Candida (e.g., Candida•antarctica, Candida•cylindracea etc.), the genus Pseudomonas (e.g., Pseudomonas•fluorescens, Pseudomonas•sp., Pseudomonas•cepacia etc.), the genus Alcaligenes (e.g., Alcaligenes•sp.), the genus Aspergillus (e.g., Aspergillus•niger etc.), and the genus Rhizopus (e.g., Rhizopus•delemar, Rhizopus•oryzae etc.).

While these lipases are obtained by culturing the microorganisms producing them and the like, commercially available products can be preferably used. Examples of such commercially available lipases include immobilized enzymes such as Novozyme 435 (manufactured by Novozyme), Lipase AK (manufactured by Amano Pharmaceutical Co., Ltd.), Lipase PL (manufactured by Meito Sangyo Co., Ltd.), Lipase QL (manufactured by Meito Sangyo Co., Ltd.) and the like.

The amount of lipase to be used is generally 0.01- to 10-fold weight, preferably generally 0.03- to 5-fold weight, relative to the alcohol derivative (II) or aliphatic alcohol (V) to be used.

The fatty acid component and/or an ester form thereof corresponding to alcohol derivative (II) may be, in addition to fatty acid (IIIa) (free form), in the forms of various fatty acid derivatives such as fatty acid ester (IIIb), triglyceride (IIIc) and the like, as well as carboxylic acid derivative (IV) may be in a form of carboxylate (IV') (hereinafter to be collectively abbreviated as fatty acid etc.).

The fatty acid etc. may be used alone or a combination of two or more kinds thereof may be used. When two or more kinds of fatty acid (IIIa) and ester forms thereof are used, the amounts thereof to be used can be converted based on the number of moles of substituent (IIIa') contained therein.

The amount of fatty acid etc. to be used may be 1.05- to 20-fold mol relative to alcohol derivative (II) or aliphatic alcohol (V) to be used, or the proportion of fatty acid etc. may be increased.

The solvent to be used is not particularly limited as long as it does not inhibit the reaction and, for example, ketone solvents such as acetone, 3-methyl-2-butanone, ethylmethylketone and the like; ether solvents such as dioxane, tetrahydrofuran, t-butyl methyl ether, diethyl ether and the like; nitrile solvents such as acetonitrile and the like; halogen solvents such as chloroform, methylene chloride and the like; hydrocarbon solvents such as hexane, heptane, toluene and the like; and the like can be mentioned. Among these, acetone and tetrahydrofuran are preferable. The amount of the solvent to be used is generally 50- to 500-fold weight, preferably generally 50- to 100-fold weight, relative to alcohol derivative (II) or aliphatic alcohol (V) to be used.

To suppress hydrolysis of produced compound (I') by lipase, the solvent to be used is preferably subjected to a dehydrating treatment in advance with a dehydrating agent such as molecular sieve, anhydrous magnesium sulfate and the like.

In addition, when fatty acid (IIIa) or carboxylic acid derivative (IV) is used, the reaction is preferably performed with the addition of a dehydrating agent, since water is produced with the progress of the reaction.

The amount of the dehydrating agent to be used is generally 10- to 100-fold weight, preferably generally 50- to 100-fold weight, relative to alcohol derivative (II) or aliphatic alcohol (V) to be used.

The reaction time is preferably about 3 to 24 hr. This depends on the reaction temperature, whose range is 25° C. to 70° C.

While a method of dehydration condensation reaction of alcohol derivative (II) or aliphatic alcohol (V) and fatty acid etc. by lipase using a solvent has been described above, the object ester derivative can be produced even without using a solvent. That is, when the reaction is performed under the above-mentioned reaction conditions without adding a solvent and a dehydrating agent, the resulting water is rapidly removed from the system, and an ester derivative can be produced at a yield equivalent to or not less than the yield obtained using a solvent and a dehydrating agent. Furthermore, the reaction can be accelerated by removing generated water by reducing the pressure.

The obtained compound (I') can be isolated and purified according to a conventional method. For example, compound (I') can be isolated by separating and recovering lipase by filtration, salting out and the like, and then purified by extraction, concentration, crystallization, chromatography and the like.

EXAMPLES

While the present invention is concretely explained in the following by referring to Examples and Experimental Examples, it is not limited to these Examples. In the following Examples, the structures of synthesized compounds were identified by nuclear magnetic resonance spectrum (Bruker AVANCE400 (400 MHz)). GC-MS was performed using Hewlett-Packard Development Company, L.P., 5890SERIESII, 5972SERIES and 7673CONTROLLER.

Production Example 1

Synthesis of 8-methylnonanoic Acid

A 500 ml three-neck flask provided with a thermometer was purged with argon, and CuBr (481 mg, 3.36 mmol) was added. NMP (43.1 ml, 449 mmol) was added at room temperature and allowed to dissolve, and the reaction vessel was cooled to −20° C. THF (10 ml) was added thereto, and 6-bromo-n-hexanoic acid ethyl ester (25.0 g, 112 mmol) was added dropwise (inside temperature −8° C.). After stirring for 10 min, a solution (160 ml) of isobutylmagnesium bromide in THF prepared separately was slowly added dropwise over 60 min.

At 90 min from the completion of the dropwise addition, 10% aqueous ammonium chloride solution (120 ml) was slowly added dropwise to quench the reaction, and the mixture was extracted with n-hexane (120 ml). The n-hexane layer was washed with 10% aqueous ammonium chloride solution (100 ml), water (100 ml) and saturated brine (50 ml). The n-hexane layer was dried over anhydrous magnesium sulfate and filtered. The filtrate was concentrated under reduced pressure to give a crude product (24.2 g) of 8-methylnonanoic acid ethyl ester as a pale-yellow oil. The purity was measured by GC-MS and found to be 97.5%.

$^1$H-NMR (CDCl$_3$,δ): 0.860 (6H, d, J=6.63 Hz), 1.13-1.33 (11H, m), 1.48-1.64 (3H, m), 2.28 (2H, t, J=7.55 Hz), 4.12 (2H, q, J=7.13 Hz)

$^{13}$C-NMR (CDCl$_3$,δ): 14.60, 22.98, 25.36, 27.56, 28.30, 29.54, 29.89, 34.75, 39.31, 60.47, 174.2.

22.2 g from the obtained 8-methylnonanoic acid ethyl ester was placed in a 500 ml egg plant-shaped flask and dissolved in ethanol (77 ml). A 2M aqueous NaOH solution (77 ml, 154 mmol) was added dropwise at room temperature over 5 min. After the completion of the dropwise addition, the mixture was stirred with heating in an oil bath at 60° C. for 90 min. After confirmation of the disappearance of the starting materials by TLC, the mixture was cooled to room temperature.

Ethanol was concentrated under reduced pressure, and the residue was partitioned between water (40 ml) and t-butyl methyl ether (80 ml). The aqueous layer was further separated and washed twice with t-butyl methyl ether (80 ml). Then the aqueous layer was acidified by slowing adding 2M aqueous HCl solution (120 ml), and the mixture was extracted with n-hexane (80 ml). The n-hexane layer was washed with water (80 ml+40 ml) and saturated brine (40 ml), and the n-hexane layer was dried over anhydrous magnesium sulfate and filtered. The filtrate was concentrated under reduced pressure to give 17.3 g of 8-methylnonanoic acid as a pale-yellow oil. 15.3 g thereof was distilled under reduced pressure to give 12.7 g of 8-methylnonanoic acid as a pale-yellow oil. The purity was measured by GC-MS and found to be not less than 99.9%. Total yield from 6-bromo-n-hexanoic acid ethyl ester: 81%.

$^1$H-NMR (CDCl$_3$,δ): 0.862 (6H, d, J=6.64 Hz), 1.14-1.17 (2H, m), 1.26-1.35 (6H, m), 1.48-1.65 (3H, m), 2.35 (2H, t, J=7.52 Hz). $^{13}$C-NMR (CDCl$_3$,δ): 22.95, 25.04, 27.55, 28.12, 29.47, 29.88, 34.51, 39.31, 181.0.

GC-MS: M=172.

Production Example 2

Synthesis of 8-methyl-1-nonanol

LAH (lithium aluminum hydride, 1.10 g, 29.0 mmol) was suspended in ether (50 ml), and the slurry was kept at 0° C. Thereto was slowly added dropwise a solution of 8-methylnonanoic acid ethyl ester (5.81 g, 29.0 mmol) in ether (20 ml). After the completion of the dropwise addition, the slurry was stirred at room temperature for 2 hr and 10% aqueous potassium hydrogen sulfate solution (50 ml) was slowly added to the reaction mixture. Ether (100 ml) was further added, and the aqueous layer was separated from the organic layer. The organic layer was washed with saturated brine (50 ml), and dried over anhydrous magnesium sulfate. Magnesium sulfate was filtered off, and the filtrate was concentrated under reduced pressure. The obtained residue was distilled under reduced pressure (60 to 65° C./2 mmHg) to give 8-methyl-1-nonanol (4.27 g, 27.0 mmol) as a colorless oil.

$^1$H-NMR (CDCl$_3$,δ): 0.86 (6H, d, J=6.60 Hz), 1.12-1.20 (2H, m), 1.20-1.40 (8H, m), 1.50-1.65 (3H, m), 3.64 (2H, t, J=6.64 Hz).

Example 1

Synthesis of Homovanillyl 8-methylnonanoate (Compound I)

Homovanillyl alcohol (769 mg, 4.57 mmol), 8-methylnonanoic acid (751 mg, 4.35 mmol) and Novozyme 435 (51 mg) were measured and placed in a flask (25 ml). The mixture was stirred with heating in an oil bath at 50° C. for 16 hr without plugging the flask. After stirring with heating for 2 to 3 hr, attachment of water onto the upper wall of the flask was observed. The reaction mixture was allowed to cool to room temperature, ethyl acetate (25 ml) was added, and Novozyme 435 and the precipitated insoluble material were removed by filtration. Ethyl acetate (50 ml) was added to the filtrate, and the mixture was washed with 5% aqueous citric acid solution (25 ml×2), saturated brine (25 ml), 5% aqueous sodium hydrogen carbonate solution (25 ml×2) and saturated brine (25 ml) and dried over anhydrous magnesium sulfate. Magnesium sulfate was filtered off, and the filtrate was concentrated under reduced pressure. The residue was developed by PTLC (preparative thin layer chromatography) (n-hexane: ethyl acetate=3:1), and silica gel containing the object product was stirred with ethyl acetate (100 ml) for 30 min for extraction. The silica gel was filtered off, and the filtrate was concentrated under reduced pressure to give homovanillyl 8-methylnonanoate (1.31 g, yield 93.2%) as a colorless oil.

$^1$H-NMR (CDCl$_3$,δ): 0.86 (6H, d, J=6.60 Hz), 1.10-1.35 (8H, m), 1.48-1.65 (3H, m), 2.23-2.35 (2H, m), 2.80-2.90 (2H, m), 3.87 (3H, s), 4.20-4.30 (2H, m), 5.54 (1H, brs), 6.65-6.90 (3H, m).

Example 2

Synthesis of 3-(3-methoxy-4-hydroxyphenyl)propyl 8-methylnonanoate (Compound J)

3-(3-Methoxy-4-hydroxyphenyl)propyl alcohol (833 mg, 4.57 mmol), 8-methylnonanoic acid (753 mg, 4.35 mmol) and Novozyme 435 (51 mg) were measured and placed in a flask (25 ml). The mixture was stirred with heating in an oil bath at 50° C. for 16 hr while reducing the pressure by an aspirator. The reaction mixture was allowed to cool to room temperature, n-hexane (25 ml) was added, and Novozyme 435 and the precipitated insoluble material were removed by filtration. N-hexane (50 ml) was added, and the mixture was washed with 5% aqueous citric acid solution (25 ml×2), saturated brine (25 ml), 5% aqueous sodium hydrogen carbonate solution (25 ml×2) and saturated brine (25 ml), and dried over anhydrous magnesium sulfate. Magnesium sulfate was filtered off, and the filtrate was concentrated under reduced pressure. The residue was developed by PTLC (n-hexane:ethyl acetate=3:1), and silica gel containing the object product was stirred with ethyl acetate (100 ml) for 30 min for extraction. The silica gel was filtered off, and the filtrate was concentrated under reduced pressure to give 3-(3-methoxy-4-hydroxyphenyl)propyl 8-methylnonanoate (1.40 g, yield 95.4%) as a colorless oil.

$^1$H-NMR (CDCl$_3$,δ): 0.86 (6H, d, J=6.60 Hz), 1.10-1.20 (2H, m), 1.20-1.38 (6H, m), 1.45-1.60 (1H, m), 1.58-1.65 (2H, m), 1.88-2.00 (2H, m), 2.30 (2H, t, J=7.44 Hz), 2.61 (2H, t, J=7.32 Hz), 3.88 (3H, s), 4.09 (2H, t, J=6.56 Hz), 5.49 (1H, s), 6.65-6.68 (2H, m), 6.83 (1H, d, J=5.2 Hz).

Example 3

Synthesis of 8-methylnonyl Homovanillate (Compound K)

8-Methyl-1-nonanol (752 mg, 4.74 mmol), homovanillic acid (907 mg, 4.98 mmol) and Novozyme 435 (100 mg) were measured and placed in a flask (25 ml). Toluene (5 ml) and anhydrous magnesium sulfate (1 g) were added, and the mixture was stirred with heating in an oil bath at 50° C. for 16 hr. The reaction mixture was allowed to cool to room temperature, toluene (25 ml) was added, and Novozyme 435 and the precipitated insoluble material were removed by filtration. Toluene (50 ml) was added, and the mixture was washed with 5% aqueous sodium hydrogen carbonate solution (25 ml×2) and saturated brine (25 ml) and dried over anhydrous magnesium sulfate. Magnesium sulfate was filtered off, and the filtrate was concentrated under reduced pressure. The residue was developed by PTLC (chloroform:n-hexane:ethyl acetate=1:1:1), and silica gel containing the object product was stirred with ethyl acetate (100 ml) for 30 min for extraction. The silica gel was filtered off, and the filtrate was concentrated under reduced pressure to give 8-methylnonyl homovanillate (1.25 g, yield 81.5%) as a colorless oil.

$^1$H-NMR (CDCl$_3$,δ): 0.86 (6H, d, J=6.64 Hz), 1.12-1.35 (10H, m), 1.45-1.65 (3H, m), 3.53 (2H, s), 3.88 (3H, s), 4.08 (2H, t, J=6.76 Hz), 5.56 (1H, s), 6.73-6.88 (3H, m).

Example 4

Synthesis of 8-methylnonyl 3-(4-hydroxy-3-methoxyphenyl)propionate (Compound L)

8-Methyl-1-nonanol (752 mg, 4.74 mmol), 3-(4-hydroxy-3-methoxyphenyl)propionic acid (977 mg, 4.98 mmol) and Novozyme 435 (100 mg) were measured and placed in a flask (25 ml). Toluene (5 ml) and anhydrous magnesium sulfate (1 g) were added, and the mixture was stirred with heating in an oil bath at 50° C. for 16 hr. The reaction mixture was allowed to cool to room temperature, toluene (25 ml) was added, and Novozyme 435 and the precipitated insoluble material were removed by filtration. Toluene (50 ml) was added, and the mixture was washed with 5% aqueous sodium hydrogen carbonate solution (25 ml×3) and saturated brine (25 ml) and dried over anhydrous magnesium sulfate. Magnesium sulfate was filtered off, and the filtrate was concentrated under reduced pressure. The residue was developed by PTLC (chloroform:n-hexane:ethyl acetate=1:1:1), and silica gel containing the object product was stirred with ethyl acetate (100 ml) for 30 min for extraction. The silica gel was filtered off, and the filtrate was concentrated under reduced pressure to give 8-methylnonyl 3-(4-hydroxy-3-methoxyphenyl)propionate (1.22 g, yield 76.2%) as a colorless oil.

$^1$H-NMR (CDCl$_3$,δ): 0.86 (6H, d, J=6.62 Hz), 1.12-1.35 (10H, m), 1.45-1.65 (3H, m), 2.59 (2H, t, J=7.36 Hz), 2.28 (2H, t, J=7.56 Hz), 3.92 (3H, s), 4.06 (2H, t, J=6.76 Hz), 5.49 (1H, s), 6.65-6.71 (2H, m), 6.82 (1H, d, J=7.86 Hz).

Example 5

Synthesis of n-decanyl Ferulate (Compound Q)

n-Decanol (1.58 g, 10.0 mmol), ferulic acid (1.94 g, 10.0 mmol) and triphenylphosphine (2.88 g, 11.0 mmol) were dissolved in THF (20 ml), and DIAD (40% solution of diisopropyl azodicarboxylate in toluene, 5.56 g, 11.0 mmol) was added to the solution. The reaction mixture was stirred at room temperature for 16 hr and concentrated under reduced pressure. Ethyl acetate (100 ml) was added to the residue, and the mixture was washed with 5% aqueous citric acid solution (25 ml×3) and saturated brine (25 ml) and dried over anhydrous magnesium sulfate. Magnesium sulfate was filtered off, and the filtrate was concentrated under reduced pressure. The residue was developed by PTLC (n-hexane:ethyl acetate=2:1), and silica gel containing the object product was stirred with ethyl acetate (100 ml) for 30 min for extraction. The silica gel was filtered off, and the filtrate was concentrated under reduced pressure to give n-decanyl ferulate (2.55 g, yield 76.2%) as a colorless oil.

$^1$H-NMR (CDCl$_3$,δ): 0.88 (3H, t, J=6.80 Hz), 1.20-1.43 (14H, m), 1.65-1.75 (2H, m), 3.93 (3H, s), 4.19 (2H, t, J=6.76 Hz), 5.86 (1H, s), 6.29 (1H, d, J=15.88 Hz), 6.91 (1H, d, J=8.16 Hz), 7.03-7.09 (2H, m), 7.60 (1H, d, J=15.92 Hz).

Example 6

Synthesis of homovanillyl 7-methyloctanoate (Compound I-1)

In the same manner as in the aforementioned Example 1, the compound was obtained as a colorless oil (yield 82.7%).

$^1$H-NMR (CDCl$_3$,δ): 0.86 (6H, d, J=6.64 Hz), 1.13-1.19 (2H, m), 1.25-1.32 (2H, m), 1.48-1.62 (3H, m), 2.29 (2H, t, J=7.54 Hz), 2.86 (2H, t, J=7.14 Hz), 3.88 (3H, s), 4.25 (2H, t, J=7.14 Hz), 6.70-6.72 (2H, m), 6.83-6.85 (1H, m).

Example 7

Synthesis of homovanillyl 6-methylheptanoate (Compound I-2)

In the same manner as in the aforementioned Example 1, the compound was obtained as a colorless oil (yield 90.5%).

¹H-NMR (CDCl₃, δ): 0.86 (6H, d, J=6.64 Hz), 1.12-1.17 (2H, m), 1.27 (4H, 5, J=3.73 Hz), 1.51 (1H, 7, J=6.63 Hz), 1.56-1.64 (2H, m), 2.28 (2H, t, J=7.54 Hz), 2.86 (2H, t, J=7.14 Hz), 3.88 (3H, s), 4.25 (2H, t, J=7.14 Hz), 6.70-6.72 (2H, m), 6.83-6.85 (1H, m).

Example 8

Synthesis of homovanillyl 5-methylhexanoate (Compound I-3)

In the same manner as in the aforementioned Example 1, the compound was obtained as a colorless oil (yield 83.3%).
¹H-NMR (CDCl₃, δ): 0.87 (6H, d, J=6.60 Hz), 1.14-1.20 (2H, m), 1.48-1.64 (3H, m), 2.27 (2H, t, J=7.56 Hz), 2.86 (2H, t, J=7.12 Hz), 3.88 (3H, s), 4.25 (2H, t, J=7.14 Hz), 6.70-6.72 (2H, m), 6.83-6.85 (1H, m).

Example 9

Synthesis of 3-(3-methoxy-4-hydroxyphenyl)propyl 7-methyloctanoate (Compound J-1)

In the same manner as in the aforementioned Example 2, the compound was obtained as a colorless oil (yield 85.4%).
¹H-NMR (CDCl₃, δ): 0.86 (6H, d, J=6.60 Hz), 1.15-1.23 (2H, m), 1.28-1.32 (4H, m), 1.45-1.59 (1H, m), 1.60-1.69 (2H, m), 1.90-1.94 (2H, m), 2.31 (2H, t, J=7.54 Hz), 2.61 (2H, t, J=7.68 Hz), 3.88 (3H, s), 4.09 (2H, t, J=6.58 Hz), 6.66-6.68 (2H, m), 6.83 (1H, d, J=8.52 Hz).

Example 10

Synthesis of 3-(3-methoxy-4-hydroxyphenyl)propyl 6-methylheptanoate (Compound J-2)

In the same manner as in the aforementioned Example 2, the compound was obtained as a colorless oil (yield 89.3%).
¹H-NMR (CDCl₃, δ): 0.87 (6H, d, J=6.64 Hz), 1.15-1.21 (2H, m), 1.28-1.39 (2H, m), 1.49-1.65 (3H, m), 1.88-1.94 (2H, m), 2.31 (2H, t, J=7.52 Hz), 2.61 (2H, t, J=7.68 Hz), 3.88 (3H, s), 4.09 (2H, t, J=6.58 Hz), 6.66-6.68 (2H, m), 6.83 (1H, d, J=8.48 Hz).

Example 11

Synthesis of 3-(3-methoxy-4-hydroxyphenyl)propyl 5-methylhexanoate (Compound J-3)

In the same manner as in the aforementioned Example 2, the compound was obtained as a colorless oil (yield 89.7%).
¹H-NMR (CDCl₃, δ): 0.89 (6H, d, J=6.60 Hz), 1.19-1.24 (2H, m), 1.50-1.69 (3H, m), 1.90-1.94 (2H, m), 2.29 (2H, t, J=7.54 Hz), 2.61 (2H, t, J=7.68 Hz), 3.87 (3H, s), 4.09 (2H, t, J=6.56 Hz), 6.67-6.68 (2H, m), 6.83 (1H, d, J=8.52 Hz).

Example 12

Synthesis of 3-(3-methoxy-4-hydroxyphenyl)propyl 4-methylpentanoate (Compound J-4)

In the same manner as in the aforementioned Example 2, the compound was obtained as a colorless oil (yield 71.2%).
¹H-NMR (CDCl₃, δ): 0.91 (6H, d, J=6.36 Hz), 1.50-1.67 (3H, m), 1.90-1.94 (2H, m), 2.31 (2H, t, J=7.68 Hz), 2.61 (2H, t, J=7.66 Hz), 3.87 (3H, s), 4.09 (2H, t, J=6.56 Hz), 6.67-6.68 (2H, m), 6.83 (1H, d, J=8.48 Hz)

Example 13

Synthesis of 3-(3-methoxy-4-hydroxyphenyl)propyl n-hexanoate (Compound J-5)

In the same manner as in the aforementioned Example 2, the compound was obtained as a colorless oil (yield 88.1%).
¹H-NMR (CDCl₃, δ): 0.90 (3H, t, J=7.02 Hz), 1.27-1.33 (4H, m), 1.63 (2H, 5, J=7.52 Hz), 1.90-1.94 (2H, m), 2.30 (2H, t, J=7.56 Hz), 2.61 (2H, t, J=7.66 Hz), 3.87 (3H, s), 4.09 (2H, t, J=6.58 Hz), 5.56 (1H, s), 6.66-6.68 (2H, m), 6.83 (1H, d, J=8.52 Hz).

Example 14

Synthesis of 7-methyloctyl homovanillate (Compound K-1)

In the same manner as in the aforementioned Example 3, the compound was obtained as a colorless oil (yield 96.8%).
¹H-NMR (CDCl₃, δ): 0.86 (6H, d, J=6.60 Hz), 1.11-1.19 (2H, m), 1.20-1.39 (6H, m), 1.48-1.67 (3H, m), 3.53 (2H, s), 3.88 (3H, s), 4.08 (2H, t, J=6.72 Hz), 6.77-6.86 (3H, m).

Example 15

Synthesis of (S)-(+)-6-methyloctyl homovanillate (Compound K-2)

In the same manner as in the aforementioned Example 3, the compound was obtained as a colorless oil (yield 95.0%).
¹H-NMR (CDCl₃, δ): 0.82-0.87 (6H, m), 1.06-1.19 (1H, m), 1.23-1.35 (8H, m), 1.58-1.65 (2H, m), 3.53 (2H, s), 3.88 (3H, s), 4.08 (2H, t, J=6.74 Hz), 6.77-6.86 (3H, m).

Example 16

Synthesis of 6-methylheptyl Homovanillate (Compound K-3)

In the same manner as in the aforementioned Example 3, the compound was obtained as a colorless oil (yield 93.8%).
¹H-NMR (CDCl₃, δ): 0.85-0.87 (6H, m), 1.12-1.18 (2H, m), 1.26-1.30 (4H, m), 1.45-1.66 (3H, m), 3.53 (2H, s), 3.88 (3H, s), 4.08 (2H, t, J=6.74 Hz), 6.77-6.86 (3H, m).

Example 17

Synthesis of 7-methyloctyl 3-(4-hydroxy-3-methoxyphenyl)propionate (Compound L-1)

In the same manner as in the aforementioned Example 4, the compound was obtained as a colorless oil (yield 84.5%).
¹H-NMR (CDCl₃, δ): 0.86 (6H, d, J=6.64 Hz), 1.13-1.18 (2H, m), 1.25-1.33 (6H, m), 1.47-1.63 (3H, m), 2.57-2.61

(2H, m), 2.88 (2H, t, J=7.76 Hz), 3.86 (3H, s), 4.06 (2H, t, J=6.74 Hz), 5.49 (1H, s), 6.67-6.71 (2H, m), 6.83 (1H, d, J=7.88 Hz).

Example 18

Synthesis of 6-methylheptyl 3-(4-hydroxy-3-methoxyphenyl)propionate (Compound L-2)

In the same manner as in the aforementioned Example 4, the compound was obtained as a colorless oil (yield 79.9%).
$^1$H-NMR (CDCl$_3$,δ): 0.86 (6H, d, J=6.64 Hz), 1.12-1.18 (2H, m), 1.25-1.32 (4H, m), 1.47-1.62 (3H, m), 2.57-2.61 (2H, m), 2.88 (2H, t, J=7.74 Hz), 3.87 (3H, s), 4.06 (2H, t, J=6.76 Hz), 5.49 (1H, s), 6.68-6.71 (2H, m), 6.83 (1H, d, J=7.88 Hz).

Example 19

Synthesis of 5-methylhexyl 3-(4-hydroxy-3-methoxyphenyl)propionate (compound L-3)

In the same manner as in the aforementioned Example 4, the compound was obtained as a colorless oil (yield 88.2%).
$^1$H-NMR (CDCl$_3$,δ): 0.87 (6H, d, J=6.60 Hz), 1.15-1.20 (2H, m), 1.27-1.35 (2H, m), 1.47-1.62 (3H, m), 2.57-2.61 (2H, m), 2.88 (2H, t, J=7.76 Hz), 3.87 (3H, s), 4.06 (2H, t, J=6.74 Hz), 5.53 (1H, s), 6.68-6.71 (2H, m), 6.83 (1H, d, J=7.88 Hz).

Example 20

Synthesis of (S)-(+)-6-methyloctyl 3-(4-hydroxy-3-methoxyphenyl)propionate (Compound L-4)

In the same manner as in the aforementioned Example 4, the compound was obtained as a colorless oil (yield 87.3%).
$^1$H-NMR (CDCl$_3$,δ): 0.83-0.87 (6H, m), 1.07-1.16 (2H, m), 1.22-1.36 (6H, m), 1.58 (2H, 5, J=6.75 Hz), 2.59 (2H, t, J=7.76 Hz), 2.88 (2H, t, J=7.76 Hz), 3.86 (3H, s), 4.06 (2H, t, J=6.74 Hz), 5.53 (1H, s), 6.68-6.71 (2H, m), 6.82 (1H, d, J=7.92 Hz).

Example 21

Synthesis of 8-methylnonyl Ferulate (Compound Q-1)

In the same manner as in the aforementioned Example 5, the compound was obtained as a colorless oil (yield 82.8%).
$^1$H-NMR (CDCl$_3$,δ): 0.86 (6H, d, J=5.92 Hz), 1.13-1.18 (2H, m), 1.26-1.43 (8H, m), 1.47-1.59 (1H, m), 1.70 (2H, 5, J=7.06 Hz), 3.96 (3H, s), 4.19 (2H, t, J=6.74 Hz), 6.29 (1H, d, J=15.88 Hz), 6.91 (1H, d, J=8.16 Hz), 7.03-7.08 (2H, m), 7.61 (1H, d, J=15.92 Hz).

Example 22

Synthesis of 7-methyloctyl Ferulate (Compound Q-2)

In the same manner as in the aforementioned Example 5, the compound was obtained as a colorless oil (yield 77.0%).
$^1$H-NMR (CDCl$_3$,δ): 0.86-0.88 (6H, m), 1.15-1.26 (2H, m), 1.27-1.43 (6H, m), 1.47-1.59 (1H, m), 1.70 (2H, 5, J=7.11 Hz), 3.93 (3H, s), 4.19 (2H, t, J=6.74 Hz), 6.29 (1H, d, J=15.88 Hz), 6.92 (1H, d, J=8.16 Hz), 7.03-7.09 (2H, m), 7.61 (1H, d, J=15.92 Hz).

Example 23

Synthesis of 6-methylheptyl Ferulate (Compound Q-3)

In the same manner as in the aforementioned Example 5, the compound was obtained as a colorless oil (yield 66.1%).
$^1$H-NMR (CDCl$_3$,δ): 0.86-0.88 (6H, m), 1.17-1.25 (2H, m), 1.26-1.42 (4H, m), 1.48-1.59 (1H, m), 1.70 (2H, 5, J=7.02 Hz), 3.91 (3H, s), 4.19 (2H, t, J=6.74 Hz), 6.29 (1H, d, J=15.88 Hz), 6.91 (1H, d, J=8.16 Hz), 7.02-7.08 (2H, m), 7.61 (1H, d, J=15.88 Hz).

Experimental Example 1

Stability of Compound

As mentioned above, the reaction yields of the compounds of respective Examples were determined by applying the products obtained by a condensation reaction to PTLC and stirring the silica gel containing the object compound with ethyl acetate for 30 min, followed by filtration and concentration under reduced pressure. Since the condensation reaction proceeds at a conversion rate of not less than 90% for all compounds, the recovery rate (yield) of each compound is considered to reflect stability upon contact of the compound with the silica gel. Hence, improvement in the stability of the compound of the present invention can be measured by comparing the recovery rate after contacting the compound of the present invention with the silica gel with the recovery rate of capsinoid after similar operation.
[Experimental Method] Isolation And Purification of Vanillyl 8-methylnonanoate by PTLC Using vanillyl alcohol (1.70 g, 11.0 mmol) instead of homovanillyl alcohol, and n-decanoic acid (1.72 g, 10 mmol) instead of 8-methylnonanoic acid in Example 1, similar reaction was performed. The residue was purified by PTLC to find that the yield of the obtained vanillyl decanoate was 1.33 g (4.31 mmol, 43.1%), and vanillyl decanoate was decomposed (i.e., unstabilized) by the contact with silica gel. In contrast, the isolation yield of homovanillyl 8-methylnonanoate obtained by similar operation was 93.2% as mentioned above, suggesting that homovanillyl 8-methylnonanoate is far stabler than vanillyl decanoate even upon contact with silica gel. In addition, since good isolation yields were obtained in Examples 2 to 23 where isolation and purification were similarly performed by PTLC, it is clear that the compound of the present invention is superior to capsinoids in the stability.
$^1$H-NMR (CDCl$_3$,δ): 0.87 (t, 3H, J=7.1 Hz), 1.18-1.30 (m, 12H), 1.55-1.65 (m, 2H), 2.33 (t, 2H, J=7.7 Hz), 3.90 (s, 3H), 5.03 (s, 2H), 5.64 (br, 1H), 6.80-6.90 (m, 3H).

Experimental Example 2

Measurement of External Blood Circulation Enhancing Action

The compound of each Example, capsinoid derivative and capsaicin were compared for vasodilatory effect using auricle of hairless mouse.
[Test method] A sample was applied to the right ear of hairless mouse (HR-1, female), and a control was applied to the left ear. Presence or absence of red spots development was visually observed, and evaluated according to the following indices.
○: clear red spots is confirmed
Δ: weak red spots is confirmed
x: no development of red spots
Sample:
(1) vanillyl alcohol (5 wt % solution in liquid paraffin, 5 wt % solution in ethanol)
(2) capsaicin (1 wt % and 5 wt % solutions in liquid paraffin, 5 wt %, 0.5 wt %, 0.05 wt % and 0.005 wt % solutions in ethanol)
(3) capsiate (1 wt % and 5 wt % solutions in liquid paraffin, 5% solution in ethanol)
(4) dihydrocapsiate (1 wt % and 5 wt % solutions in liquid paraffin)
(5) nordihydrocapsiate (1 wt % and 5 wt % solutions in liquid paraffin)
(6) homovanillyl 8-methylnonanoate (compound I, 5 wt % solution in liquid paraffin)
(7) 3-(3-methoxy-4-hydroxyphenyl)propyl 8-methylnonanoate (compound J, 5 wt % solution in liquid paraffin, 5 wt % solution in ethanol)
(8) 8-methylnonyl homovanillate (compound K, 5 wt % solution in liquid paraffin)
(9) 8-methylnonyl 3-(4-hydroxy-3-methoxyphenyl)propionate (compound L, 5 wt % solution in liquid paraffin)
(10) homovanillyl 7-methyloctanoate (compound I-1, 5 wt % solution in liquid paraffin, 5 wt % solution in ethanol)
(11) homovanillyl 6-methylheptanoate (compound I-2, 5 wt % solution in liquid paraffin (partially crystallized), 5 wt % solution in ethanol)
(12) homovanillyl 5-methylhexanoate (compound I-3, 5 wt % suspension in liquid paraffin, 5 wt % solution in ethanol)
(13) 3-(3-methoxy-4-hydroxyphenyl)propyl 7-methyloctanoate (compound J-1, 1 wt % solution in liquid paraffin, 5 wt % suspension in liquid paraffin, 5 wt % solution in ethanol)
(14) 3-(3-methoxy-4-hydroxyphenyl)propyl 6-methylheptanoate (compound J-2, 1 wt % and 5 wt % solutions in liquid paraffin, 5 wt % solution in ethanol)
(15) 3-(3-methoxy-4-hydroxyphenyl)propyl 5-methylhexanoate (compound J-3, 1 wt % solution in liquid paraffin, 5 wt % suspension in liquid paraffin, 5 wt % solution in ethanol)
(16) 3-(3-methoxy-4-hydroxyphenyl)propyl 4-methylpentanoate (compound J-4, 1 wt % solution in liquid paraffin, 5 wt % solution in liquid paraffin (partially precipitated), 5 wt % solution in ethanol)
(17) 3-(3-methoxy-4-hydroxyphenyl)propyl n-hexanoate (compound J-5, 1 wt % solution in liquid paraffin, 5 wt % solution in liquid paraffin, 5 wt % solution in ethanol)
(18) 7-methyloctyl homovanillate (compound K-1, 1 wt % solution in liquid paraffin, 5 wt % suspension in liquid paraffin, 0.5 wt %, 0.05 wt % and 0.005 wt % solutions in ethanol)
(19) (S)-(+)-6-methyloctyl homovanillate (compound K-2, 1 wt % solution in liquid paraffin, 5 wt % suspension in liquid paraffin, 0.5 wt %, 0.05 wt % and 0.005 wt % solutions in ethanol)
(20) 6-methylheptyl homovanillate (compound K-3, 1 wt % solution in liquid paraffin, 5 wt % suspension in liquid paraffin, 0.5 wt %, 0.05 wt % and 0.005 wt % solutions in ethanol)
(21) 7-methyloctyl 3-(4-hydroxy-3-methoxyphenyl)propionate (compound L-1, 1 wt % solution in liquid paraffin, 5 wt % suspension in liquid paraffin, 5 wt % solution in ethanol)
(22) 6-methylheptyl 3-(4-hydroxy-3-methoxyphenyl)propionate (compound L-2, 1 wt % and 5 wt % solutions in liquid paraffin, 5 wt % solution in ethanol)
(23) 5-methylhexyl 3-(4-hydroxy-3-methoxyphenyl)propionate (compound L-3, 1 wt % and 5 wt % solutions in liquid paraffin, 5 wt % solution in ethanol)
(24) (S)-(+)-6-methyloctyl 3-(4-hydroxy-3-methoxyphenyl)propionate (compound L-4, 1 wt % solution in liquid paraffin, 5 wt % suspension in liquid paraffin, 5 wt % solution in ethanol)
(25) 8-methylnonyl ferulate (compound Q-1, 5 wt % solution in liquid paraffin, 5 wt % solution in ethanol)
(26) 7-methyloctyl ferulate (compound Q-2, 5 wt % suspension in liquid paraffin, 5 wt % solution in ethanol)
(27) 6-methylheptyl ferulate (compound Q-3, 5 wt % suspension in liquid paraffin, 5 wt % solution in ethanol)
Control: liquid paraffin, ethanol The results are shown in Tables 2 to 4. The compounds K, K-1, K-2, K-3, L, L-1, L-2, L-3 and L-4 newly synthesized by the present inventors were confirmed to show a potent vasodilatory effect. Particularly, compounds K-1, K-2 and K-3 were confirmed to show a potent vasodilatory effect. In addition, compounds I, I-1, I-2, I-3, J-1, J-2, J-3, J-4 and J-5 were also confirmed to show a weak blood circulation enhancing effect.

TABLE 2

Vasodilatory effect for hairless mouse - 1

| sample | 5 wt % (liquid paraffin) | 5 wt % (liquid paraffin) | note |
|---|---|---|---|
| vanillyl alcohol | x | — | Application of 5 wt %: no blood circulation enhancing effect |
| capsaicin | ○ | ○ | Application of 1 wt %: red spots were observed even after lapse of 2 hr |
| capsiate | ○ | Δ | Application of 5 wt %: weak red spots were observed even after lapse of 90 min |
| dihydrocapsiate | ○ | Δ | Application of 5 wt %: weak red spots were observed even after lapse of 90 min |
| nordihydrocapsiate | ○ | Δ | Application of 5 wt %: weak red spots were observed even after lapse of 90 min |
| compound I | Δ | — | blood circulation enhancing effect was weak and disappeared in 1 hr |
| compound I-1 | x | — | sparingly soluble, thus red spots were not observed |
| compound I-2 | x | — | sparingly soluble, thus red spots were not observed |
| compound I-3 | x | — | sparingly soluble, thus red spots were not observed |
| compound J | x | — | Application of 5 wt %: no blood circulation enhancing effect |
| compound J-1 | Δ | x | Application of 5 wt %: red spots disappeared in 1 hr |
| compound J-2 | Δ | x | Application of 5 wt %: red spots disappeared in 1 hr |
| compound J-3 | Δ | x | Application of 5 wt %: red spots disappeared in 1 hr |
| compound J-4 | Δ | x | Application of 5 wt %: red spots disappeared in 1 hr |
| compound J-5 | Δ | x | Application of 5 wt %: red spots disappeared in 1 hr |

TABLE 2-continued

Vasodilatory effect for hairless mouse - 1

| sample | 5 wt % (liquid paraffin) | 5 wt % (liquid paraffin) | note |
| --- | --- | --- | --- |
| compound K | ○ | — | Application of 5 wt %: weak red spots were observed even after lapse of 2 hr |
| compound K-1 | ○ | ○ | Application of 5 wt %: red spots were observed even after lapse of 90 min |
| compound K-2 | ○ | ○ | Application of 5 wt %: red spots were observed even after lapse of 90 min |
| compound K-3 | ○ | ○ | Application of 5 wt %: red spots were observed even after lapse of 90 min |
| compound L | ○ | — | Application of 5 wt %: red spots were observed even after lapse of 90 min |
| compound L-1 | ○ | Δ | Application of 5 wt %: red spots disappeared in 1 hr |
| compound L-2 | ○ | Δ | Application of 5 wt %: red spots disappeared in 1 hr |
| compound L-3 | ○ | Δ | Application of 5 wt %: red spots disappeared in 1 hr |
| compound L-4 | ○ | ○ | Application of 5 wt %: weak red spots were observed even after lapse of 1 hr |
| compound Q-1 | x | — | Application of 5 wt %: no blood circulation enhancing effect |
| compound Q-2 | x | — | Application of 5 wt %: no blood circulation enhancing effect |
| compound Q-3 | x | — | Application of 5 wt %: no blood circulation enhancing effect |

TABLE 3

Vasodilatory effect on hairless mouse - 2

| sample | 5 wt % (ethanol) | note |
| --- | --- | --- |
| vanillyl alcohol | x | |
| capsaicin | ○ | Strong red spots were observed. |
| capsiate | ○ | Clear red spots were observed. |
| dihydro-capsiate | — | |
| nor-dihydro-capsiate | — | |
| compound I | — | |
| compound I-1 | Δ | Weak red spots were observed at 20 min after application. Intensity of red spots at 30 min later was I-1 > I-2 > I-3. |
| compound I-2 | Δ | |
| compound I-3 | Δ | |
| compound J | x | |
| compound J-1 | ○ | Weak red spots were observed at 10 min after application. Red spots almost disappeared at 30 min later. Intensity of red spots was J-1 > J-2 > J-3 > J-4 > J-5. |
| compound J-2 | ○ | |
| compound J-3 | ○ | |
| compound J-4 | ○ | |
| compound J-5 | Δ | |
| compound K | — | |
| compound K-1 | — | |
| compound K-2 | — | |
| compound K-3 | — | |
| compound L | — | |
| compound L-1 | ○ | Red spots were observed at 5 min after application. At 1 hr later, thin red spots remained. L-4 showed strong red spots after 1 hr. |
| compound L-2 | ○ | |
| compound L-3 | ○ | |
| compound L-4 | ○ | |
| compound Q-1 | x | |
| compound Q-2 | x | |
| compound Q-3 | x | |

TABLE 4

Vasodilatory effect for hairless mouse - 3

| sample | 0.5 wt % (ethanol) | 0.05 wt % (ethanol) | 0.005 wt % (ethanol) |
| --- | --- | --- | --- |
| capsaicin | ○ | ○ | Δ |
| K-1 | ○ | ○ | Δ |
| K-2 | ○ | ○ | Δ |
| K-3 | ○ | ○ | Δ |

Industrial Applicability

Since the compound of the present invention has an external blood circulation enhancing action, it is useful as an active ingredient of cosmetic compositions. In addition, the compound can be preferably used as a pharmaceutical agent such as sympathetic activation agent and the like, a diet food material and the like.

This application is based on a patent application No. 2006-084298 filed in Japan, the contents of which are incorporated in full herein by this reference.

Although the present invention have been presented or described by referring to preferred embodiments of this invention, it will, however, be understood by those of ordinary skill in the art that various modifications may be made to the forms and details without departing from the scope of the invention as set forth in the appended claims. All patents, patent publications and other publications indicated or cited in the Specification are hereby incorporated in their entireties by reference.

The invention claimed is:

1. A compound represented by formula (I)

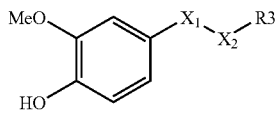

wherein $X_1$ is a methylene group, an ethylene group, a trimethylene group or a vinylene group, $X_2$ is a divalent group represented by formula A or B

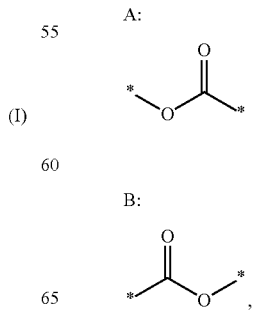

, and

R3 is a group represented by formula (IIIa')

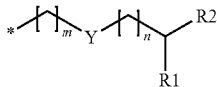
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that (1) when $X_1$ is an ethylene group and $X_2$ is a divalent group represented by formula A, then R3 is not an n-octyl group;

(2) when $X_1$ is an ethylene group and $X_2$ is a divalent group represented by formula B, then R3 is not an n-propyl group, an n-butyl group, or an n-tridecanyl group;

(3) when $X_1$ is a methylene group, then $X_2$ is not a divalent group represented by formula A;

(4) when $X_1$ is a methylene group and $X_2$ is a divalent group represented by formula B, then R3 is not a straight chain alkyl group having a carbon number of 3 to 12;

(5) when $X_1$ is a vinylene group and $X_2$ is a divalent group represented by formula B, then R3 is not a straight chain alkyl group, a 3-methylbutyl group, a 6-methylheptyl group, or a 3-hexenyl group;

(6) when $X_1$ is a vinylene group, then $X_2$ is not a divalent group represented by formula A; and (7) when $X_1$ is a trimethylene group and $X_2$ is a divalent group represented by formula A, then R3 is not an n-propyl group or an n-butyl group.

2. A compound of claim 1, wherein m and n are each an integer of 0 to 7, which satisfy m+n=2 to 8.

3. A compound of claim 1, wherein $X_1$ is an ethylene group or a trimethylene group, and $X_2$ is a divalent group represented by formula A.

4. A compound of claim 1, wherein $X_1$ is a methylene group or an ethylene group, and $X_2$ is a divalent group represented by formula B.

5. A compound of claim 1, wherein $X_1$ is a methylene group, and $X_2$ is a divalent group represented by formula B.

6. A compound of claim 2, wherein Y is an ethylene group, and R1 and R2 are each independently a methyl group or an ethyl group.

7. An external blood circulation enhancer comprising at least one compound represented by formula (I')

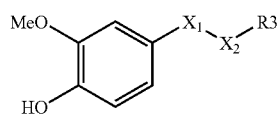
(I')

wherein $X_1$ is a methylene group, an ethylene group, a trimethylene group or a vinylene group, $X_2$ is a divalent group represented by formula A or B

A:

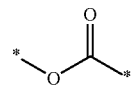

B:

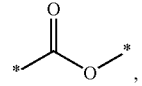

and

R3 is a group represented by formula (IIIa')

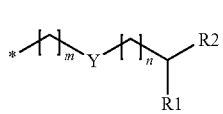
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that (1) when $X_1$ is an ethylene group and $X_2$ is a divalent group represented by formula A, then R3 is not an n-octyl group;

(2) when $X_1$ is an ethylene group and $X_2$ is a divalent group represented by formula B, then R3 is not an n-propyl group, an n-butyl group, or an n-tridecanyl group;

(3) when $X_1$ is a methylene group, then $X_2$ is not a divalent group represented by formula A;

(4) when $X_1$ is a methylene group and $X_2$ is a divalent group represented by formula B, then R3 is not a straight chain alkyl group having a carbon number of 3 to 12;

(5) when $X_1$ is a vinylene group and $X_2$ is a divalent group represented by formula B, then R3 is not a straight chain alkyl group, a 3-methylbutyl group, a 6-methylheptyl group, or a 3-hexenyl group;

(6) when $X_1$ is a vinylene group, then $X_2$ is not a divalent group represented by formula A; and (7) when $X_1$ is a trimethylene group and $X_2$ is a divalent group represented by formula A, then R3 is not an n-propyl group or an n-butyl group.

8. An external blood circulation enhancer of claim 7, wherein m and n are each an integer of 0 to 7, which satisfy m+n=2 to 8.

9. An external blood circulation enhancer of claim 7, wherein $X_1$ is an ethylene group or a trimethylene group, and $X_2$ is a divalent group represented by formula A.

10. An external blood circulation enhancer of claim 7, wherein $X_1$ is a methylene group or an ethylene group, and $X_2$ is a divalent group represented by formula B.

11. An external blood circulation enhancer of claim 7, wherein $X_1$ is a methylene group, and $X_2$ is a divalent group represented by formula B.

12. An external blood circulation enhancer of claim 7, wherein Y is an ethylene group, and R1 and R2 are each independently a methyl group or an ethyl group.

13. A cosmetic composition comprising an external blood circulation enhancer of claim 7.

14. A sympathetic activation pharmaceutical composition comprising at least one compound represented by formula (I')

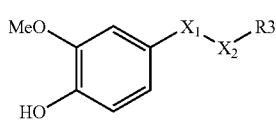

(I')

wherein $X_1$ is a methylene group, an ethylene group, a trimethylene group or a vinylene group, $X_2$ is a divalent group represented by formula A or B

A:

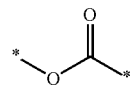

B:

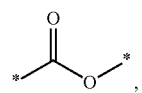

and
R3 is a group represented by formula (IIIa')

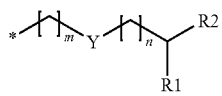

(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that
(1) when $X_1$ is an ethylene group and $X_2$ is a divalent group represented by formula A, then R3 is not an n-octyl group;
(2) when $X_1$ is an ethylene group and $X_2$ is a divalent group represented by formula B, then R3 is not an n-propyl group, an n-butyl group, or an n-tridecanyl group;
(3) when $X_1$ is a methylene group, then $X_2$ is not a divalent group represented by formula A;
(4) when $X_1$ is a methylene group and $X_2$ is a divalent group represented by formula B, then R3 is not a straight chain alkyl group having a carbon number of 3 to 12;
(5) when $X_1$ is a vinylene group and $X_2$ is a divalent group represented by formula B, then R3 is not a straight chain alkyl group, a 3-methylbutyl group, a 6-methylheptyl group, or a 3-hexenyl group;
(6) when $X_1$ is a vinylene group, then $X_2$ is not a divalent group represented by formula A; and
(7) when $X_1$ is a trimethylene group and $X_2$ is a divalent group represented by formula A, then R3 is not an n-propyl group or an n-butyl group.

15. A sympathetic activation pharmaceutical composition of claim 14, wherein m and n are each an integer of 0 to 7, which satisfy m+n=2 to 8.

16. A sympathetic activation food composition comprising at least one compound represented by formula (I')

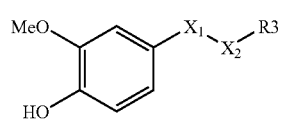

(I')

wherein $X_1$ is a methylene group, an ethylene group, a trimethylene group or a vinylene group, $X_2$ is a divalent group represented by formula A or B

A:

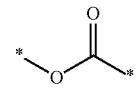

B:

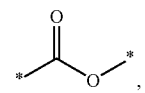

and
R3 is a group represented by formula (IIIa')

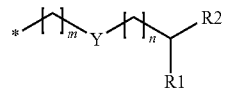

(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that
(1) when $X_1$ is an ethylene group and $X_2$ is a divalent group represented by formula A, then R3 is not an n-octyl group;
(2) when $X_1$ is an ethylene group and $X_2$ is a divalent group represented by formula B, then R3 is not an n-propyl group, an n-butyl group, or an n-tridecanyl group;
(3) when $X_1$ is a methylene group, then $X_2$ is not a divalent group represented by formula A;
(4) when $X_1$ is a methylene group and $X_2$ is a divalent group represented by formula B, then R3 is not a straight chain alkyl group having a carbon number of 3 to 12;
(5) when $X_1$ is a vinylene group and $X_2$ is a divalent group represented by formula B, then R3 is not a straight chain alkyl group, a 3-methylbutyl group, a 6-methylheptyl group, or a 3-hexenyl group;
(6) when $X_1$ is a vinylene group, then $X_2$ is not a divalent group represented by formula A; and
(7) when $X_1$ is a trimethylene group and $X_2$ is a divalent group represented by formula A, then R3 is not an n-propyl group or an n-butyl group.

17. A sympathetic activation food composition of claim 16, wherein m and n are each an integer of 0 to 7, which satisfy m+n=2 to 8.

18. A method of producing a compound according to claim 1,
comprising:
(a) subjecting an alcohol compound represented by the following formula (II)

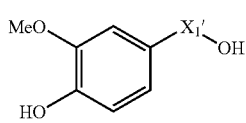 (II)

wherein $X_1'$ is an ethylene group or a trimethylene group, to a dehydration condensation reaction with at least one member selected from the group consisting of:

(i) a fatty acid represented by formula (IIIa)

 (IIIa)

wherein R3a is a group represented by formula (IIIa')

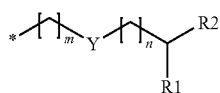 (IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that (1') when $X_1'$ is an ethylene group, then R3a is not an n-octyl group; and (7') when $X_1'$ is a trimethylene group, then R3a is not an n-propyl group or an n-butyl group;

(ii) a fatty acid ester represented by formula (IIIb)

 (IIIb)

wherein R4 is an aliphatic hydrocarbon group and R3a is as defined above; and (iii) a triglyceride represented by formula (IIIc)

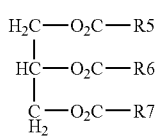 (IIIc)

wherein at least one of R5, R6 and R7 is as defined in the above-mentioned R3a, and the rest are each independently an aliphatic hydrocarbon group, in the presence of an enzyme catalyst; or (b) subjecting a carboxylic acid compound represented by formula (IV)

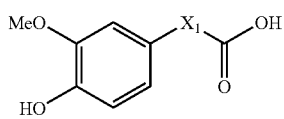 (IV)

wherein $X_1$ is as defined above, or a carboxylate represented by formula (IV')

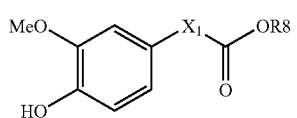 (IV')

wherein $X_1$ is as defined above and R8 is an aliphatic hydrocarbon group, to a dehydration condensation reaction with an aliphatic alcohol represented by formula (V)

 (V)

wherein R3b is a group represented by formula (IIIa')

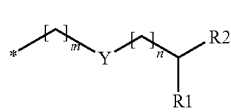 (IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that (2') when $X_1$ is an ethylene group, then R3b is not an n-propyl group, an n-butyl group, or an n-tridecanyl group;

(4') when $X_1$ is a methylene group, then R3b is not a straight chain alkyl group having a carbon number of 3 to 12; and (5') when $X_1$ is a vinylene group, then R3b is not a straight chain alkyl group, a 3-methylbutyl group, a 6-methylheptyl group, or a 3-hexenyl group, in the presence of an enzyme catalyst.

19. A method of producing a compound according to claim 1, comprising:

(a) subjecting an alcohol compound represented by formula (II)

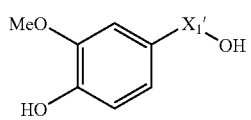 (II)

wherein $X_1'$ is an ethylene group or a trimethylene group, to a chemical condensation reaction with a fatty acid represented by formula (IIIa)

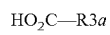 (IIIa)

wherein R3a is a group represented by formula (IIIa')

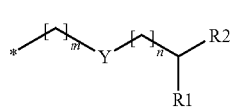 (IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group, provided that
(1') when $X_1'$ is an ethylene group, then R3a is not an n-octyl group; and
(7') when $X_1'$ is a trimethylene group, then R3a is not an n-propyl group or an n-butyl group,
using a dehydrating condensation agent; or
(b) subjecting a carboxylic acid compound represented by formula (IV)

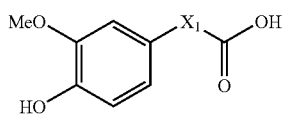
(IV)

wherein $X_1$ is as defined above, to a chemical condensation reaction with an aliphatic alcohol represented by formula (V)

HO—R3b     (V)

wherein R3b is a group represented by the following formula (IIIa')

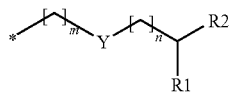
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group,
provided that
(2') when $X_1$ is an ethylene group, then R3b is not an n-propyl group, an n-butyl group, or an n-tridecanyl group;
(4') when $X_1$ is a methylene group, then R3b is not a straight chain alkyl group having a carbon number of 3 to 12; and
(5') when $X_1$ is a vinylene group, then R3b is not a straight chain alkyl group, a 3-methylbutyl group, a 6-methylheptyl group, or a 3-hexenyl group,
using a dehydrating condensation agent.

20. A method of producing a compound represented by formula (I")

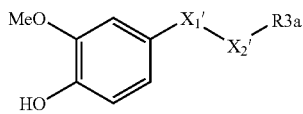
(I")

wherein
$X_1'$ is an ethylene group or a trimethylene group,
$X_2'$ is a divalent group represented by formula A A:
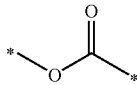

R3a is a group represented by formula (IIIa')

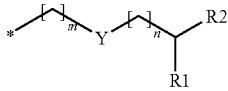
(IIIa')

wherein Y is an ethylene group or a vinylene group, m and n are each an integer of 0 to 7, which satisfy m+n=0 to 8, and R1 and R2 are each independently a hydrogen atom, a methyl group or an ethyl group,
provided that
(1') when $X_1'$ is an ethylene group, then R3a is not an n-octyl group; and
(7') when $X_1'$ is a trimethylene group, then R3a is not an n-propyl group or an n-butyl group,
which comprises
converting a fatty acid represented by formula (IIIa)

$HO_2C$—R3a     (IIIa)

wherein R3a is as defined above, to an acid chloride, and reacting said acid chloride with an alcohol compound represented by formula (II)

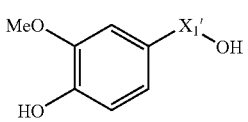
(II)

wherein $X_1'$ is as defined above,
in the presence of a base.

21. A pharmaceutical composition, which comprises at least one compound according to claim 1 and at least one pharmaceutically acceptable carrier.

22. An external blood circulation enhancer according to claim 7, which further comprises at least one further blood circulation enhancer.

23. An external blood circulation enhancer according to claim 22, which further comprises at least one further blood circulation enhancer selected from the group consisting of powdered capsicum, capsicum tincture, capsicum essence, capsaicin, homocapsaicin, homodihydrocapsaicin, vanillyl nonanamide, ginger extract, capsicum extract, nicotinic acid, sophorae radix extract, Astragalus root extract, zingiber siccatum extract, safflower extract, Japanese pepper extract, Salvia miltiorrhiza extract, panacis japonici rhizoma extract, ginseng extract, and γ-aminobutyric acid.

24. A cosmetic composition according to claim 13, further comprising at least one ingredient selected from the group consisting of an oily base, a surfactant, a polymeric substance, a solvent, a powder substance, an antioxidant, an anti-inflammatory agent, a UV absorber, a skin-lightening agent, a cellular stimulant, a moisturizing agent, a metal chelating agent, a dye, a flavor, and a transdermal absorption enhancer.

25. A sympathetic activation pharmaceutical composition according to claim 14, further comprising at least one pharmaceutically acceptable carrier.

26. A sympathetic activation food composition according to claim 16, further comprising at least one food additive selected from the group consisting of a fruit juice, dextrin, a cyclic oligosaccharide, a saccharide, a polysaccharide, an acidulant, a flavor, a Hiki cha powder, an emulsifier, collagen, powdered milk, agar, a vitamin, egg shell calcium, calcium pantothenate, royal jelly, propolis, honey, a dietary fibre, Agaricus subrufescens, chitin, chitosan, a flavonoid, a carotenoid, lutein, an herbal medicine, chondroitin, and an amino acid.

* * * * *

SEQUENCE LISTING

```
<160> NUMBER OF SEQ ID NOS: 2

<210> SEQ ID NO 1
<211> LENGTH: 2520
<212> TYPE: DNA
<213> ORGANISM: Homo sapiens
<220> FEATURE:
<221> NAME/KEY: CDS
<222> LOCATION: (1)..(2520)

<400> SEQUENCE: 1
```

```
atg aag aaa tgg agc agc aca gac ttg ggg gca gct gcg gac cca ctc      48
Met Lys Lys Trp Ser Ser Thr Asp Leu Gly Ala Ala Ala Asp Pro Leu
1               5                   10                  15 caa aag gac acc tgc cca gac ccc ctg gat gga gac cct aac tcc agg      96
Gln Lys Asp Thr Cys Pro Asp Pro Leu Asp Gly Asp Pro Asn Ser Arg
            20                  25                  30 cca cct cca gcc aag ccc cag ctc tcc acg gcc aag agc cgc acc cgg     144
Pro Pro Pro Ala Lys Pro Gln Leu Ser Thr Ala Lys Ser Arg Thr Arg
        35                  40                  45 ctc ttt ggg aag ggt gac tcg gag gag gct ttc ccg gtg gat tgc cct     192
Leu Phe Gly Lys Gly Asp Ser Glu Glu Ala Phe Pro Val Asp Cys Pro
    50                  55                  60 cac gag gaa ggt gag ctg gac tcc tgc ccg acc atc aca gtc agc cct     240
His Glu Glu Gly Glu Leu Asp Ser Cys Pro Thr Ile Thr Val Ser Pro
65                  70                  75                  80 gtt atc acc atc cag agg cca gga gac ggc ccc acc ggt gcc agg ctg     288
Val Ile Thr Ile Gln Arg Pro Gly Asp Gly Pro Thr Gly Ala Arg Leu
                85                  90                  95 ctg tcc cag gac tct gtc gcc gcc agc acc gag aag acc ctc agg ctc     336
Leu Ser Gln Asp Ser Val Ala Ala Ser Thr Glu Lys Thr Leu Arg Leu
            100                 105                 110 tat gat cgc agg agt atc ttt gaa gcc gtt gct cag aat aac tgc cag     384
Tyr Asp Arg Arg Ser Ile Phe Glu Ala Val Ala Gln Asn Asn Cys Gln
        115                 120                 125 gat ctg gag agc ctg ctg ctc ttc ctg cag aag agc aag aag cac ctc     432
Asp Leu Glu Ser Leu Leu Leu Phe Leu Gln Lys Ser Lys Lys His Leu
    130                 135                 140 aca gac aac gag ttc aaa gac cct gag aca ggg aag acc tgt ctg ctg     480
Thr Asp Asn Glu Phe Lys Asp Pro Glu Thr Gly Lys Thr Cys Leu Leu
145                 150                 155                 160 aaa gcc atg ctc aac ctg cac gac gga cag aac acc acc atc ccc ctg     528
Lys Ala Met Leu Asn Leu His Asp Gly Gln Asn Thr Thr Ile Pro Leu
                165                 170                 175 ctc ctg gag atc gcg cgg caa acg gac agc ctg aag gag ctt gtc aac     576
Leu Leu Glu Ile Ala Arg Gln Thr Asp Ser Leu Lys Glu Leu Val Asn
            180                 185                 190 gcc agc tac acg gac agc tac tac aag ggc cag aca gca ctg cac atc     624
Ala Ser Tyr Thr Asp Ser Tyr Tyr Lys Gly Gln Thr Ala Leu His Ile
        195                 200                 205 gcc atc gag aga cgc aac atg gcc ctg gtg acc ctc ctg gtg gag aac     672
Ala Ile Glu Arg Arg Asn Met Ala Leu Val Thr Leu Leu Val Glu Asn
    210                 215                 220 gga gca gac gtc cag gct gcg gcc cat ggg gac ttc ttt aag aaa acc     720
Gly Ala Asp Val Gln Ala Ala Ala His Gly Asp Phe Phe Lys Lys Thr
225                 230                 235                 240 aaa ggg cgg cct gga ttc tac ttc ggt gaa ctg ccc ctg tcc ctg gcc     768
Lys Gly Arg Pro Gly Phe Tyr Phe Gly Glu Leu Pro Leu Ser Leu Ala
                245                 250                 255 gcg tgc acc aac cag ctg ggc atc gtg aag ttc ctg ctg cag aac tcc     816
Ala Cys Thr Asn Gln Leu Gly Ile Val Lys Phe Leu Leu Gln Asn Ser
            260                 265                 270 tgg cag acg gcc gac atc agc gcc agg gac tcg gtg ggc aac acg gtg     864
Trp Gln Thr Ala Asp Ile Ser Ala Arg Asp Ser Val Gly Asn Thr Val
        275                 280                 285 ctg cac gcc ctg gtg gag gtg gcc gac aac acg gcc gac aac acg aag     912
Leu His Ala Leu Val Glu Val Ala Asp Asn Thr Ala Asp Asn Thr Lys
    290                 295                 300 ttt gtg acg agc atg tac aat gag att ctg atc ctg ggg gcc aaa ctg     960
Phe Val Thr Ser Met Tyr Asn Glu Ile Leu Ile Leu Gly Ala Lys Leu
305                 310                 315                 320
```

-continued

| | | |
|---|---|---|
| cac ccg acg ctg aag ctg gag gag ctc acc aac aag aag gga atg atg<br>His Pro Thr Leu Lys Leu Glu Glu Leu Thr Asn Lys Lys Gly Met Met<br>                      325                        330                      335 | | 1008 |
| ccg ctg gct ctg gca gct ggg acc ggg aag atc ggg gtc ttg gcc tat<br>Pro Leu Ala Leu Ala Ala Gly Thr Gly Lys Ile Gly Val Leu Ala Tyr<br>              340                        345                      350 | | 1056 |
| att ctc cag cgg gag atc cag gag ccc gag tgc agg cac ctg tcc agg<br>Ile Leu Gln Arg Glu Ile Gln Glu Pro Glu Cys Arg His Leu Ser Arg<br>            355                        360                      365 | | 1104 |
| aag ttc acc gag tgg gcc tac ggg ccc gtg cac tcg tcg ctg tac gac<br>Lys Phe Thr Glu Trp Ala Tyr Gly Pro Val His Ser Ser Leu Tyr Asp<br>   370                      375                      380 | | 1152 |
| ctg tcc tgc atc gac acc tgc gag aag aac tcg gtg ctg gag gtg atc<br>Leu Ser Cys Ile Asp Thr Cys Glu Lys Asn Ser Val Leu Glu Val Ile<br>385                      390                      395                      400 | | 1200 |
| gcc tac agc agc agc gag acc cct aat cgc cac gac atg ctc ttg gtg<br>Ala Tyr Ser Ser Ser Glu Thr Pro Asn Arg His Asp Met Leu Leu Val<br>                      405                        410                      415 | | 1248 |
| gag ccg ctg aac cga ctc ctg cag gac aag tgg gac aga ttc gtc aag<br>Glu Pro Leu Asn Arg Leu Leu Gln Asp Lys Trp Asp Arg Phe Val Lys<br>            420                        425                      430 | | 1296 |
| cgc atc ttc tac ttc aac ttc ctg gtc tac tgc ctg tac atg atc atc<br>Arg Ile Phe Tyr Phe Asn Phe Leu Val Tyr Cys Leu Tyr Met Ile Ile<br>                435                        440                      445 | | 1344 |
| ttc acc atg gct gcc tac tac agg ccc gtg gat ggc ttg cct ccc ttt<br>Phe Thr Met Ala Ala Tyr Tyr Arg Pro Val Asp Gly Leu Pro Pro Phe<br>450                      455                      460 | | 1392 |
| aag atg gaa aaa act gga gac tat ttc cga gtt act gga gag atc ctg<br>Lys Met Glu Lys Thr Gly Asp Tyr Phe Arg Val Thr Gly Glu Ile Leu<br>465                      470                      475                      480 | | 1440 |
| tct gtg tta gga gga gtc tac ttc ttt ttc cga ggg att cag tat ttc<br>Ser Val Leu Gly Gly Val Tyr Phe Phe Phe Arg Gly Ile Gln Tyr Phe<br>                        485                        490                      495 | | 1488 |
| ctg cag agg cgg ccg tcg atg aag acc ctg ttt gtg gac agc tac agt<br>Leu Gln Arg Arg Pro Ser Met Lys Thr Leu Phe Val Asp Ser Tyr Ser<br>            500                        505                      510 | | 1536 |
| gag atg ctt ttc ttt ctg cag tca ctg ttc atg ctg gcc acc gtg gtg<br>Glu Met Leu Phe Phe Leu Gln Ser Leu Phe Met Leu Ala Thr Val Val<br>                515                        520                      525 | | 1584 |
| ctg tac ttc agc cac ctc aag gag tat gtg gct tcc atg gta ttc tcc<br>Leu Tyr Phe Ser His Leu Lys Glu Tyr Val Ala Ser Met Val Phe Ser<br>            530                        535                      540 | | 1632 |
| ctg gcc ttg ggc tgg acc aac atg ctc tac tac acc cgc ggt ttc cag<br>Leu Ala Leu Gly Trp Thr Asn Met Leu Tyr Tyr Thr Arg Gly Phe Gln<br>545                      550                      555                      560 | | 1680 |
| cag atg ggc atc tat gcc gtc atg ata gag aag atg atc ctg aga gac<br>Gln Met Gly Ile Tyr Ala Val Met Ile Glu Lys Met Ile Leu Arg Asp<br>                565                        570                      575 | | 1728 |
| ctg tgc cgt ttc atg ttt gtc tac atc gtc ttc ttg ttc ggg ttt tcc<br>Leu Cys Arg Phe Met Phe Val Tyr Ile Val Phe Leu Phe Gly Phe Ser<br>            580                        585                      590 | | 1776 |
| aca gcg gtg gtg acg ctg att gaa gac ggg aag aat gac tcc ctg ccg<br>Thr Ala Val Val Thr Leu Ile Glu Asp Gly Lys Asn Asp Ser Leu Pro<br>                595                        600                      605 | | 1824 |
| tct gag tcc acg tcg cac agg tgg cgg ggg cct gcc tgc agg ccc ccc<br>Ser Glu Ser Thr Ser His Arg Trp Arg Gly Pro Ala Cys Arg Pro Pro<br>            610                        615                      620 | | 1872 |
| gat agc tcc tac aac agc ctg tac tcc acc tgc ctg gag ctg ttc aag<br>Asp Ser Ser Tyr Asn Ser Leu Tyr Ser Thr Cys Leu Glu Leu Phe Lys<br>625                      630                      635                      640 | | 1920 |

```
ttc acc atc ggc atg ggc gac ctg gag ttc act gag aac tat gac ttc      1968
Phe Thr Ile Gly Met Gly Asp Leu Glu Phe Thr Glu Asn Tyr Asp Phe
            645                 650                 655 aag gct gtc ttc atc atc ctg ctg ctg gcc tat gta att ctc acc tac      2016
Lys Ala Val Phe Ile Ile Leu Leu Leu Ala Tyr Val Ile Leu Thr Tyr
            660                 665                 670 atc ctc ctg ctc aac atg ctc atc gcc ctc atg ggt gag act gtc aac      2064
Ile Leu Leu Leu Asn Met Leu Ile Ala Leu Met Gly Glu Thr Val Asn
            675                 680                 685 aag atc gca cag gag agc aag aac atc tgg aag ctg cag aga gcc atc      2112
Lys Ile Ala Gln Glu Ser Lys Asn Ile Trp Lys Leu Gln Arg Ala Ile
            690                 695                 700 acc atc ctg gac acg gag aag agc ttc ctt aag tgc atg agg aag gcc      2160
Thr Ile Leu Asp Thr Glu Lys Ser Phe Leu Lys Cys Met Arg Lys Ala
705                 710                 715                 720 ttc cgc tca ggc aag ctg ctg cag gtg ggg tac aca cct gat ggc aag      2208
Phe Arg Ser Gly Lys Leu Leu Gln Val Gly Tyr Thr Pro Asp Gly Lys
                725                 730                 735 gac gac tac cgg tgg tgc ttc agg gtg gac gag gtg aac tgg acc acc      2256
Asp Asp Tyr Arg Trp Cys Phe Arg Val Asp Glu Val Asn Trp Thr Thr
            740                 745                 750 tgg aac acc aac gtg ggc atc atc aac gaa gac ccg ggc aac tgt gag      2304
Trp Asn Thr Asn Val Gly Ile Ile Asn Glu Asp Pro Gly Asn Cys Glu
            755                 760                 765 ggc gtc aag cgc acc ctg agc ttc tcc ctg cgg tca agc aga gtt tca      2352
Gly Val Lys Arg Thr Leu Ser Phe Ser Leu Arg Ser Ser Arg Val Ser
            770                 775                 780 ggc aga cac tgg aag aac ttt gcc ctg gtc ccc ctt tta aga gag gca      2400
Gly Arg His Trp Lys Asn Phe Ala Leu Val Pro Leu Leu Arg Glu Ala
785                 790                 795                 800 agt gct cga gat agg cag tct gct cag ccc gag gaa gtt tat ctg cga      2448
Ser Ala Arg Asp Arg Gln Ser Ala Gln Pro Glu Glu Val Tyr Leu Arg
                805                 810                 815 cag ttt tca ggg tct ctg aag cca gag gac gct gag gtc ttc aag agt      2496
Gln Phe Ser Gly Ser Leu Lys Pro Glu Asp Ala Glu Val Phe Lys Ser
            820                 825                 830 cct gcc gct tcc ggg gag aag tga                                      2520
Pro Ala Ala Ser Gly Glu Lys
            835
```

<210> SEQ ID NO 2
<211> LENGTH: 839
<212> TYPE: PRT
<213> ORGANISM: Homo sapiens

<400> SEQUENCE: 2

```
Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
                20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
        50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
            100                 105                 110
```

-continued

```
Tyr Asp Arg Arg Ser Ile Phe Glu Ala Val Ala Gln Asn Asn Cys Gln
            115                 120                 125

Asp Leu Glu Ser Leu Leu Phe Leu Gln Lys Ser Lys Lys His Leu
130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190

Ala Ser Tyr Thr Asp Ser Tyr Tyr Lys Gly Gln Thr Ala Leu His Ile
                195                 200                 205

Ala Ile Glu Arg Arg Asn Met Ala Leu Val Thr Leu Leu Val Glu Asn
            210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
                260                 265                 270

Trp Gln Thr Ala Asp Ile Ser Ala Arg Asp Ser Val Gly Asn Thr Val
            275                 280                 285

Leu His Ala Leu Val Glu Val Ala Asp Asn Thr Ala Asp Asn Thr Lys
            290                 295                 300

Phe Val Thr Ser Met Tyr Asn Glu Ile Leu Ile Leu Gly Ala Lys Leu
305                 310                 315                 320

His Pro Thr Leu Lys Leu Glu Glu Leu Thr Asn Lys Lys Gly Met Met
                325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
                355                 360                 365

Lys Phe Thr Glu Trp Ala Tyr Gly Pro Val His Ser Ser Leu Tyr Asp
            370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
                420                 425                 430

Arg Ile Phe Tyr Phe Asn Phe Leu Val Tyr Cys Leu Tyr Met Ile Ile
            435                 440                 445

Phe Thr Met Ala Ala Tyr Tyr Arg Pro Val Asp Gly Leu Pro Pro Phe
450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Arg Gly Ile Gln Tyr Phe
                485                 490                 495

Leu Gln Arg Arg Pro Ser Met Lys Thr Leu Phe Val Asp Ser Tyr Ser
                500                 505                 510

Glu Met Leu Phe Phe Leu Gln Ser Leu Phe Met Leu Ala Thr Val Val
                515                 520                 525

Leu Tyr Phe Ser His Leu Lys Glu Tyr Val Ala Ser Met Val Phe Ser
```

-continued

```
                530                 535                 540
Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
                580                 585                 590

Thr Ala Val Val Thr Leu Ile Glu Asp Gly Lys Asn Asp Ser Leu Pro
                595                 600                 605

Ser Glu Ser Thr Ser His Arg Trp Arg Gly Pro Ala Cys Arg Pro Pro
                610                 615                 620

Asp Ser Ser Tyr Asn Ser Leu Tyr Ser Thr Cys Leu Glu Leu Phe Lys
625                 630                 635                 640

Phe Thr Ile Gly Met Gly Asp Leu Glu Phe Thr Glu Asn Tyr Asp Phe
                645                 650                 655

Lys Ala Val Phe Ile Ile Leu Leu Leu Ala Tyr Val Ile Leu Thr Tyr
                660                 665                 670

Ile Leu Leu Leu Asn Met Leu Ile Ala Leu Met Gly Glu Thr Val Asn
                675                 680                 685

Lys Ile Ala Gln Glu Ser Lys Asn Ile Trp Lys Leu Gln Arg Ala Ile
                690                 695                 700

Thr Ile Leu Asp Thr Glu Lys Ser Phe Leu Lys Cys Met Arg Lys Ala
705                 710                 715                 720

Phe Arg Ser Gly Lys Leu Leu Gln Val Gly Tyr Thr Pro Asp Gly Lys
                725                 730                 735

Asp Asp Tyr Arg Trp Cys Phe Arg Val Asp Glu Val Asn Trp Thr Thr
                740                 745                 750

Trp Asn Thr Asn Val Gly Ile Ile Asn Glu Asp Pro Gly Asn Cys Glu
                755                 760                 765

Gly Val Lys Arg Thr Leu Ser Phe Ser Leu Arg Ser Ser Arg Val Ser
770                 775                 780

Gly Arg His Trp Lys Asn Phe Ala Leu Val Pro Leu Leu Arg Glu Ala
785                 790                 795                 800

Ser Ala Arg Asp Arg Gln Ser Ala Gln Pro Glu Glu Val Tyr Leu Arg
                805                 810                 815

Gln Phe Ser Gly Ser Leu Lys Pro Glu Asp Ala Glu Val Phe Lys Ser
                820                 825                 830

Pro Ala Ala Ser Gly Glu Lys
                835
```